United States Patent [19]

Abe et al.

[11] Patent Number: 4,929,623

[45] Date of Patent: May 29, 1990

[54] BENZOTHIAZOLE DERIVATIVE

[75] Inventors: Shinya Abe, Ushiku; Mitsuaki Miyamoto; Masayuki Tanaka, both of Tsukuba; Kozo Akasaka, Ushiku; Kenji Hayashi, Tsukuba; Tetsuya Kawahara, Tsukuba; Satoshi Katayama, Tsukuba; Yoshinori Sakuma, Ushiku; Takeshi Suzuki, Ushiku; Isao Yamatsu, Ushiku, all of Japan

[73] Assignee: Eisai Co., Ltd., Tokyo, Japan

[21] Appl. No.: 207,329

[22] Filed: Jun. 16, 1988

[30] Foreign Application Priority Data

Jun. 17, 1987 [JP] Japan .............................. 62-150987

[51] Int. Cl.$^5$ .................. C07D 277/82; A61K 31/425

[52] U.S. Cl. .................................... 514/293; 514/366; 514/367; 546/83; 548/150; 548/161; 548/163; 548/164; 548/162

[58] Field of Search ............... 548/161, 150, 164, 163; 546/83; 514/367, 366, 293

[56] References Cited

PUBLICATIONS

Lau, J. Org. Chem. 12, 4103 (1970).
Ulrich, J. Med. Chem. 25, 654 (1982).

*Primary Examiner*—Robert Gerstl
*Attorney, Agent, or Firm*—Birch, Stewart, Kolasch & Birch

[57] ABSTRACT

A benzothiazol compound having the formula is disclosed and is effective to inhibit the production of leukotriene. It is useful against allergy, asthma, affections of the skin, allergic rhinitis and affection of a cardiovascular system.

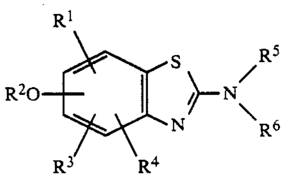

in which R20 is ester or amide and —NR5R6 is amino in variety.

27 Claims, No Drawings

BENZOTHIAZOLE DERIVATIVE

The present invention relates to a benzothiazole derivative which exhibits excellent pharmaceutical activities.

[PRIOR ART]

Asthmatic attack occurs as a result of a complicated combination of vital reactions. It is generally believed that the asthmatic attack is mainly due to stenosis of the air passage caused by various chemical mediators which are produced and liberated by an antigen-antibody reaction as a trigger.

Examples of known chemical mediators include histamine, prostaglandin, and SRS-A. Among them, SRA-A was proved to be leukotrienes $C_4$ and $D_4$ in 1979 by Professor Samuelson in Sweden. Since then, SRS-A attracted attention because of its relationship with asthmatic attack which continues for a long period of time.

Further, it was proved that the liberation of leukotrienes occurred in the skin reaction and the reaction of the nasal mucosa as well, that the inhalation of leukotrienes brought about asthmatic attack, and that the concentration of leukotrienes was significantly increased in the blood or bronchoalveolar cleaning fluid (BACF) of patients suffering from asthmatic attack. From these facts, it is believed that there is a high possibility for leukotrienes to be a key mediator of the asthmatic attack.

Hitherto, antiasthmatic agents have been developed based on a general idea that the liberation of the chemical mediator should be inhibited. Representative examples of such an antiasthmatic agent include Intal which has been put on the market since 1969. However, in the conventional antiasthmatic agents including Intal, the mediator liberation inhibitory concentration in vitro is different from that in vivo. Further, there is much unknown matter about the action mechanism, and few physicians are satisfied with the clinical effect of the conventional antiasthmatic agents. Therefore, the development of an antiasthmatic agent exhibiting an excellent clinical effect has been strongly desired.

Under these circumstances, the present inventors have made extensive and intensive studies for a long period of time with a view to developing a novel therapeutic agent for asthma which exhibits an excellent effect in clinical test as well with respect to the leukotriene production inhibitory action due to 5-lipoxygenase inhibition.

As a result, the present inventors have found that the object can be attained by the following benzothiazole derivative, which has led to the completion of the present invention.

Therefore, an object of the present invention is to provide a novel benzothiazole derivative and a pharmacologically acceptable salt thereof useful as an antiasthmatic agent. Another object of the present invention is to provide a process for preparing said compound or a pharmacologically acceptable salt thereof. A further object of the present invention is to provide a pharmaceutical comprising as an effective ingredient said compound or pharmacologically acceptable salt thereof.

(SUMMARY OF THE INVENTION)

The object compound of the present invention is a benzothiazole derivative and a pharmacologically acceptable salt thereof represented by the following general formula (I):

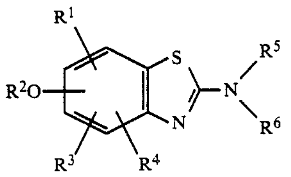

wherein $R^1$, $R^3$, and $R^4$ which may be the same or different are each a hydrogen atom, a lower alkyl group, a halogen atom, an acyl group, a hydroxyl group, a lower alkoxy group, a hydroxy lower alkyl group, a nitro group, an amino group, or a lower dialkylamino group, provided that any two of $R^1$, $R^3$, and $R^4$ may be combined together to form an aromatic ring which may consist of only carbon atoms or additionally contain a nitrogen atom, $R^2$ is a hydrogen atom, an acyl group, a group represented by the formula

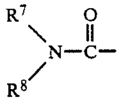

(wherein $R^7$ and $R^8$ which may be the same or different are each a hydrogen atom or a lower alkyl group), $R^5$ and $R^6$ which may be the same or different are each (1) a hydrogen atom, (2) a group represented by the formula:

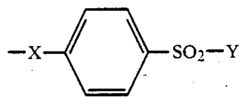

wherein X is a group represented by the formula —CO— or a group represented by the formula $—CH_2—$, and Y is a group represented by the formula

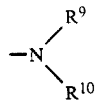

(wherein $R^9$ and $R^{10}$ which may be the same or different are each a hydrogen atom, a lower alkyl group, a halogen atom, a lower alkoxy group, a hydroxy lower alkyl group or a lower dialkyl group) or a lower alkyl group, (3) a group represented by the formula:

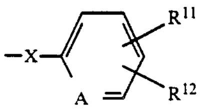

wherein A is a carbon atom or a nitrogen atom, X is a group represented by the formula —CO— or a group represented by the formula $—CH_2—$, and $R^{11}$ and $R^{12}$ which may be the same or different are each a hydrogen atom, a halogen atom, a carbamoyl group, a group represented by the formula $—COOR^{13}$ (wherein $R^{13}$ is a hydrogen atom or a lower alkyl group), a group represented by the formula

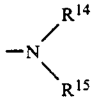

(wherein $R^{14}$ and $R^{15}$ which may be the same or different are each a hydrogen atom or a lower alkyl group), a group represented by the formula $—NH—SO_2—R^{16}$ (wherein $R^{16}$ is a lower alkyl group), or a tetrazoyl group, (4) a group represented by the formula:

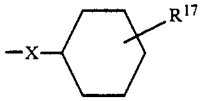

wherein X is a group represented by the formula —CO— or a group represented by the formula $—CH_2—$, and $R^{17}$ is a hydrogen atom, a hydroxyl group or a lower alkyl group, (5) a group represented by the formula:

$$—X—(CH_2)_n—Z$$

wherein X is a group represented by the formula —CO— or a group represented by the formula $—CH_2—$, n is an integer of 0 to 10, and Z is a group represented by the formula $—COOR^{18}$ (wherein $R^{18}$ is a hydrogen atom or a lower alkyl group, a group represented by the formula

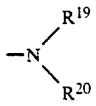

(wherein $R^{19}$ and $R^{20}$ which may be the same or different are a hydrogen atom or a lower alkyl group), a group represented by the formula $—CONHR^{21}$ (wherein $R^{21}$ is a hydrogen atom, a lower alkyl group, or a cycloalkyl group), a lower alkoxy group, a cycloalkyl group, a cyano group, or a hydroxyl group, (6) a lower alkyl group, (7) a hydroxyl lower alkyl group, (8) a lower alkenyl group, (9) a group represented by the formula:

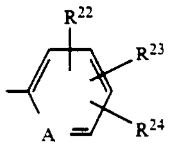

wherein A is a carbon atom or a nitrogen atom, and $R^{22}$, $R^{23}$, and $R^{24}$ which may be the same or different are each a hydrogen atom, a lower alkyl group, a lower alkoxy group, a halogen atom, an aminosulfonyl group, a group represented by the formula $—(CH_2)_a—COOR^{25}$ (wherein a is an integer of 0 to 6, and $R^{25}$ is a hydrogen atom or a lower alkyl group), a group represented by the formula $—O—(CH_2)_b—COOR^{26}$ (wherein b is an integer of 1 to 6, and $R^{26}$ is a hydrogen atom or a lower alkyl group), a group represented by the formula

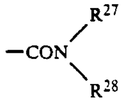

(wherein $R^{27}$ and $R^{28}$ which may be the same or different are each a hydrogen atom or a lower alkyl group), or a group represented by the formula

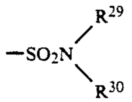

(wherein $R^{29}$ and $R^{30}$ which may be the same or different are each a hydrogen atom or a lower alkyl group, or

(10) a group represented by the formula:

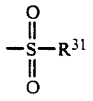

wherein $R^{31}$ is a lower alkyl group, a group represented by the formula

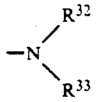

(wherein $R^{32}$ and $R^{33}$ which may be the same or different are each a hydrogen atom or a lower alkyl group), or a substituted or unsubstituted phenyl group, or

(11) $R^5$ and $R^6$ may be combined together to form a ring which may additionally contain a nitrogen atom and an oxygen atom and may be unsubstituted or substituted.

It is preferable in the definition of the benzothiazole of the invention that R5 is hydrogen and R6 is (2); R5 and R6 are hydrogen; R5 is hydrogen and R6 is (3); R5 is hydrogen and R6 is (9): R5 and R6 are (7); or the benzothiazole ring has R2O— at 6-position.

The preferably compounds include:

6-hydroxy-2-(4-sulfamoylbenzylamino)-4,5,7-trimethylbenzothiazole,
6-hydroxy-2-(4-carboxylphenylamino)-4,5,7-trimethylbenzothiazole,
6-hydroxy-2-amino-4,5,7-trimethylbenzothiazole,
6-hydroxy-2-(4-carboxylphenylamino)-5,7-diisopropylbenzothiazole,
6-hydroxy-2-(N,N-di(2-hydroxyethyl)amino-5,7-diisopropylbenzothiazole,
6-hydroxy-2-(2-pyridylmethylamino)-5,7-diisopropylbenzothiazole,
6-hydroxy-2-(4-sulfamoylbenzylamino)-5,7-dibromobenzothiazole and
4-hydroxy-2-(4-sulfamoylbenzylamino)-5,7-dibromobenzothiazole.

The invention also provides a pharmaceutical composition which comprises a therapeutically effective amount of the benzothiazole compound as defined above or a pharmacologically acceptable salt thereof and a pharmacologically acceptable carrier, a therapeutic composition for the leukotriene production-inhibitory action due to 5-lipoxygenase inhibition, which comprises a therapeutically effective amount of the benzothiazole compound as defined above or a pharmacologically acceptable salt thereof and a pharmcologically acceptable carrier and an anti-allergic agent which comprises the benzothiazole compound as defined above or a pharmacologically acceptable salt thereof.

The invention, in addition, provides a method for treating a desease of a human patient, caused by production of the leukotriene, by administering thereto a therapeutically effective amount of a benzothiazole compound as defined above or a pharmacologically acceptable salt thereof.

With respect to the compound (I) of the present invention, the term "lower alkyl group" used in the above definition of $R^1$, $R^3$, $R^4$, $R^7$, $R^8$, $R^5$, and $R^6$ in the above items (1) to (10) is intended to mean a straight-chain or branched alkyl group having 1 to 6 carbon atoms, and examples thereof include methyl, ethyl, propyl, isopropyl, butyl, isobutyl, sec-butyl, pentyl (amyl), isopenthyl, neopentyl, tert-pentyl, 1-methylbutyl, 2-methylbutyl, 1,2-dimethylpropyl, hexyl, isohexyl, 1-methylpentyl, 2-methylpentyl, 3-methylpentyl, 1,1-dimethylbutyl, 1,2-dimethylbutyl, 2,2-dimethylbutyl, 1,3-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, and 1-ethyl-2-methylpropyl groups. Among them, methyl, ethyl, propyl, isopropyl groups etc. are preferable.

The term "lower alkoxy group" used in the above definition of $R^1$, $R^3$, $R^4$, $R^5$, and $R^6$ in the above items (1) to (10) is intended to mean a straight-chain or branched alkoxy group having 1 to 6 carbon atoms, and examples thereof include methoxy, ethoxy, n-propoxy, isopropoxy, n-butoxy, isobutoxy, sec-butoxy, tert-butoxy, pentyloxy, isopentyloxy, neopentyloxy, tert-pentyloxy, 1-methylbutoxy, 2-methylbutoxy, 1,2-dimethylpropoxy, and hexyloxy groups. Among them, methoxy, ethoxy groups etc. are preferable.

The term "hydroxy lower alkyl group" used in the above definition of $R^1$, $R^3$, $R^4$, $R^5$, and $R^6$ is intended to mean a group comprising the above-defined lower alkyl group having 1 to 6 carbon atoms and a hydroxyl group bonded to any of the carbon atoms of the lower alkyl group, and preferable examples thereof include hydroxymethyl, 2-hydroxyethyl, 1-hydroxyethyl, and 3-hydroxypropyl groups.

The term "halogen atom" used in the definition of $R^9$, $R^{10}$, $R^{11}$, $R^{12}$, $R^{22}$, $R^{23}$, and $R^{24}$ which appear in the definition of $R^1$, $R^3$, $R^4$, $R^5$, and $R^6$ is intended to mean chlorine, bromine, iodine, and fluorine. Among them, chlorine and bromine are preferable.

The term "acyl group" used in the definition of $R^1$, $R^2$, $R^3$, and $R^4$ is intended to mean any acyl group derived from aliphatic, aromatic, and heretocyclic rings. Among them, preferable examples of the acyl group include lower alkanoyl groups such as formyl, acetyl, propionyl, butyryl, valeryl, isovaleryl, and pivaloyl groups; aroyl groups such as benzoyl, toluoyl, and naphthoyl groups; and heteroaroyl groups such as furoyl, nicotinoyl, and isonicotinoyl groups.

The term "lower dialkylamino group" used in the definition of $R^1$, $R^3$, $R^4$, $R^9$, and $R^{10}$ is intended to mean a lower dialkylamino group derived from the above-defined lower alkyl group. Most preferable examples of the lower dialkylamino group include a dimethylamino group.

In the definition of $R^1$, $R^3$, and $R^4$, the expression "any two of $R^1$, $R^3$, and $R^4$ may be combined together to form an aromatic ring which may consist of only carbon atoms or additionally contain a nitrogen atom" is intended to mean, for example, the formation of a benzene ring, a pyridine ring, or a pyrimidine ring by combination of carbon atoms adjacent to each other and located at the fourth to seventh positions of the phenyl ring in the benzothiazole ring.

Preferable examples thereof include:

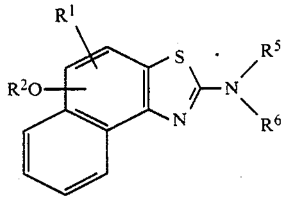

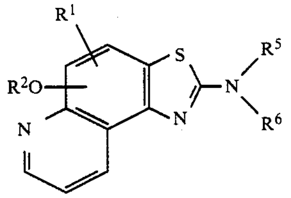

wherein $R^1$, $R^2$, $R^5$, and $R^6$ are as defined above.

In the definition of $R^2$, the term "lower alkoxycarbonyl group" is intended to mean a lower alkoxycarbonyl group derived from the above-defined lower alkoxy group having 1 to 6 carbon atoms. Preferable examples thereof include methoxycarbonyl, ethoxycarbonyl, n-propoxycarbonyl, isopropoxycarbonyl, n-butoxycarbonyl, and isobutoxycarbonyl groups.

In item (5) of the definition of $R^5$ and $R^6$, the term "cycloalkyl group" is intended to mean cyclopentyl, cyclohexyl groups etc.

In the definition of $R^5$ and $R^6$, the term "lower alkenyl group" is intended to mean a lower alkenyl group derived from the above-defined lower alkyl group having 1 to 6 carbon atoms. Preferable examples thereof include 1-propenyl, 2-butenyl, 2-methyl-1-propenyl, and 4-methyl-2-butenyl groups.

In the definition of $R^{31}$ in the above item (10) with respect to the definition of $R^5$ and $R^6$, preferable examples of the substituent with respect to the expression "substituted or unsubstituted phenyl group" include lower alkyl groups such as a methyl group, lower alkoxy groups such as a methoxy group, and a carbamoyl group.

Examples of the ring referred to in the expression "$R^5$ and $R^6$ may be combined together to form a ring which may additionally contain a nitrogen atom and an oxygen atom and may be unsubstituted or substituted" with respect to the definition of $R^5$ and $R^6$ in the above item (11) include five- and six-membered rings containing nitrogen or oxygen, such as morpholino, piperazinyl, and pyrrolidinyl groups. These rings may be unsubstituted or substituted. Examples of the substituents include lower alkyl groups having 1 to 6 carbon atoms, such as methyl and ethyl groups, a hydroxyl group, a carboxyl group, and a group represented by the formula "=O".

Among them, the following groups are most preferable:

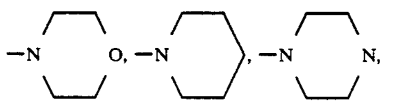

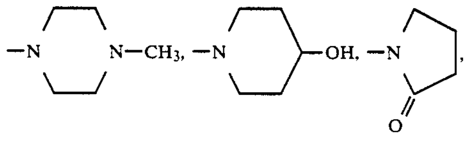

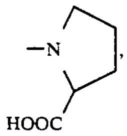

, and

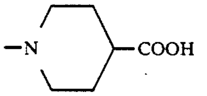

The term "pharmaceutically acceptable salt" include salts of inorganic acids, such as hydrochloride, hydrobromide, sulfate, and phosphate; those of organic acids, such as acetate, maleate, tartrate, methanesulfonate, benzenesulfonate, and toluenesulfonate; and those of amino acids such as arginine, aspartic acid, and glutamic acid. Further, certain compounds of the present invention are in the form of metallic salts such as Na, K, Ca, and Mg salts, and these metallic salts are also within the scope of the pharmacologically acceptable salt. Furthermore, some compounds of the present invention may be in the form of a hydrate. The compounds according to the present invention may have asymmetric carbon atoms when they have particular substituents so that they may be present in the form of stereoisomers. These are, of course, within the scope of the present invention.

The compound (I) of the present invention has the following structure having a benzothiazole skeleton:

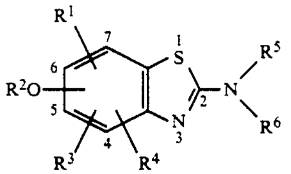
(I)

wherein $R^1$, $R^2$, $R^3$, $R^4$, $R^5$, and $R^6$ are as defined above. Specifically, the compound (I) of the present invention has a benzothiazole skeleton, and the 2-position thereof is substituted with various amino groups including a cyclic amino group. Further, it is possible for the phenyl ring constituting the benzothiazole skeleton to have up to 4 substituents. It is noted in this connection that the group represented by the formula $-OR^2$ is most preferably attached to the 6-position and $R^2$ is most preferably H.

Various amino groups represented by the formula

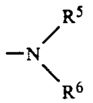

are as defined above, and preferable examples of the amino groups include a group represented by the formula

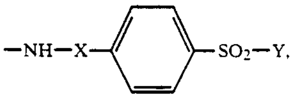

wherein X and Y are as defined above, a group represented by the formula

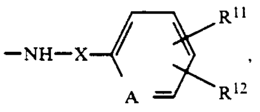

wherein X, A, $R^{11}$, and $R^{12}$ are as defined above, a group represented by the formula

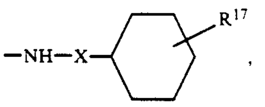

wherein X and $R^{17}$ are as defined above, a group represented by the formula $-NH-X-(CH_2)_n-Z$, wherein X, Z, and n are as defined above, a group represented by the formula

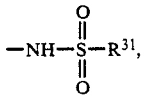

wherein $R^{31}$ is as defined above, and a group represented by formula

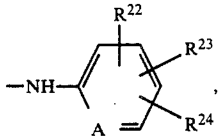

wherein A, $R^{22}$, $R^{23}$, and $R^{24}$ are as defined above. In the above-described amino groups, favorable results can be attained when X is a group represented by the formula $—CH_2—$.

Among them, the most preferable amino group is a group represented by the formula

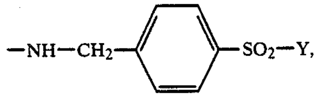

wherein Y is as defined above. Y is preferably a group represented by the formula

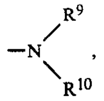

wherein $R^9$ and $R^{10}$ are as defined above.

Therefore, the characteristic features of the structure of the compound according to the present invention reside in that the phenyl ring of the benzothiazole skeleton has a group represented by the formula $—OR^2$ as one of the substituents and that the 2-position of the benzothiazole skeleton is substituted with various amino groups.

The compound of the present invention is valuable as various pharmaceuticals based on the leukotriene liberation inhibitory action, particularly as an antiallergic agent and a therapeutic and preventive agent for asthma and has a novel skeleton which has not been found in the conventional compounds exhibiting this kind of drug effect.

PROCESS

The compound of the present invention may be prepared by various processes. Representative processes for preparing the compound of the present invention will now be described.

In the general formula (I), when $R^2$ is H, i.e., when any of the 4-, 5-, 6-, and 7-positions are a hydroxyl group, it is preferred that the object substance be prepared by conducting a reaction with the hydroxyl group protected in the form of a methyl ether and conducting demethylation in the final step in which each object substance is obtained (e.g., according to the method of Process 8 which will be described later).

In the following Processes 1, 3, 5, 6, and 7, $R^{2'}$ includes a methyl group in addition to the groups defined with respect to $R^2$. When $R^{2'}$ is a methyl group, the compound is not an object compound but a compound which can be used as a starting material in any of the processes.

Process 1

In the general formula (I), when $R^5$ and $R^6$ are each a hydrogen atom, the compound of the present invention can be prepared, e.g., by the following process:

(II)

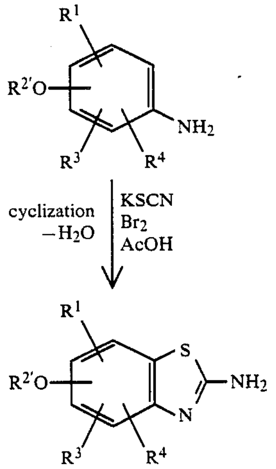

(III)

Specifically, a compound represented by the general formula (II) is cyclized according to an ordinary method to prepare a compound represented by the general formula (III) which is one of the object substances.

In this reaction, the compound (II) having an amino group is cyclized by making use of potassium thiocyanate and bromine. For example, this reaction is conducted according to the method described in Beilstein, 27(2), p.334. Examples of a reaction solvent include an acetic acid-water solvent system in which the ratio of acetic acid to water is 1:1 to 95:5.

The reaction temperature usually ranges from 0° C. to room temperature.

Process 2

When the object compound represented by the general formula (I) is a compound represented by the following formula:

(IV)

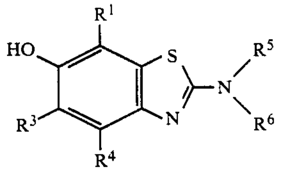

such a compound can be prepared also by the following cyclization:

(V)

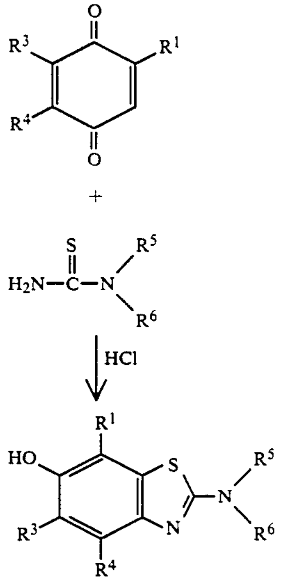

(VI)

(IV)

wherein $R^1$, $R^3$, $R^4$, $R^5$, and $R^6$ are as defined above.

In this process, a compound (IV) is prepared by allowing 1,4-benzoquinone (V) to condense with thiourea (VI) in the presence of concentrated hydrochloric acid according to the method described in J. Org. Chem., 35, 4103 (1970).

Methanol, ethanol or the like is used as the solvent, and the reaction temperature ranges from 0° C. to a temperature at which the solvent is refluxed.

Process 3 (amidation by acyl halide process)

In the general formula (I), when $R^6$ is a group represented by the following formula

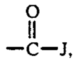

wherein J is as defined above or a group represented by the formula —SO2—$R^{31}$, wherein $R^{31}$ is as defined above, the compound of the present invention can be prepared also by the following process:

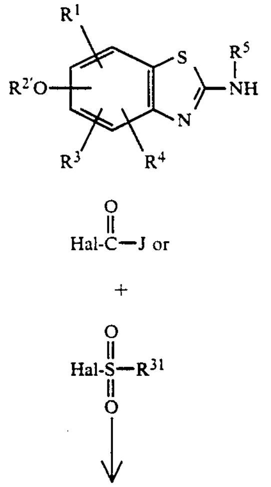

(VII)

(VIII)

or (IX)

-continued

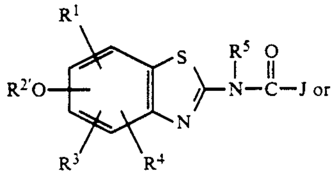

(X)

or

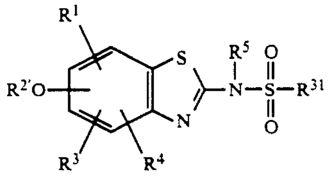

(XI)

wherein $R^1$, $R^{2'}$, $R^3$, $R^4$, $R^5$, and $R^{31}$ are as defined above, J is the same group as that described in the above items (2) to (5) with respect to the definition of $R^5$ and $R^6$, excpet that J is free from a group represented by the formula —X—, and Hal is a halogen.

Specifically, this process comprises an amidation reaction, i.e., reacting a compound (VII) having an amino group with an acyl halide (VIII) or (IX) preferably in the presence of a base to prepare an amide compound (X) or (XI).

An acyl chloride and an acyl bromide are used as the acyl halide. Examples of the base include carbonates and bicarbonates of alkali metals such as sodium bicarbonate, potassium carbonate, and sodium carbonate, alkali hydroxides such as sodium hydroxide and potassium hydroxide, and organic bases such as triethylamine, pyridine, and diethylaniline, and further sodium hydroxide.

A suitable solvent may be selected from those which do not take part in the reaction.

Process 4 (amidation by acid anhydride)

In the general formula (I), when $R^6$ is a group represented by the following formula

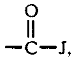

wherein J is as defined above, the compound of the present invention can be prepared also by the following process:

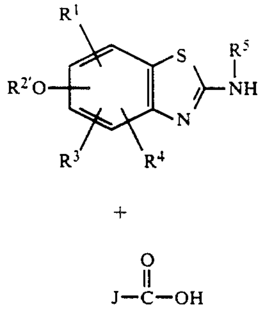

(VII)

(XII)

-continued

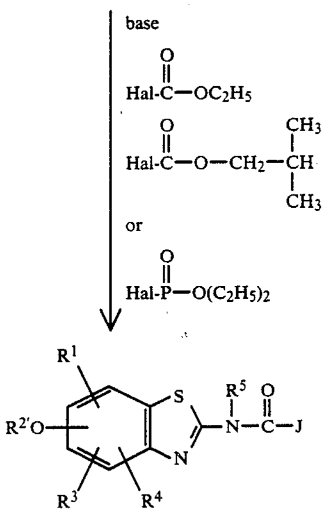

(XIII)

wherein $R^1$, $R^{2'}$, $R^3$, $R^4$, $R^5$, and J are as defined above.

This process comprises reacting a compound (VII) having an amino group with ethyl chlorocarbonate, isobutyl chlorocarbonate, or diethyl chlorophosphate to prepare a mixed acid anhydride and reacting the obtained anhydride with a carboxylic acid (XII) to prepare an amide compound (XIII).

Any base may be used as the base. Further, any solvent which does not take part in the reaction may be used as the solvent. Preferable examples of the solvent include tetrahydrofuran and N,N-dimethylformamide. The reaction temperature is preferably 0° C. in the step of preparing a mixed acid anhydride and, in the subsequent steps, ranges from 0° C. to a temperature at which the solvent is refluxed.

Process 5 (production via Schiff base)

In the general formula (I), when a group represented by the formula

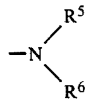

is a group represented by the formula —NH—$CH_2$—J, wherein J is as defined above, the compound of the present invention can be prepared also by the following process:

(XIV)

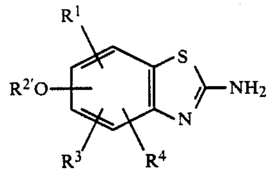

+

J—CHO (XV)

-continued

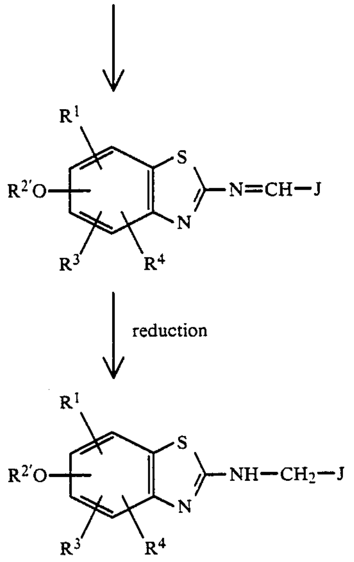

(XVI)

(XVII)

wherein $R^1$, $R^{2'}$, $R^3$, $R^4$, and J are as defined above.

In this process, a compound (XIV) having an amino group is reacted with an aldehyde (XV) while removing formed water, thereby preparing a Schiff base. In this case, any solvent which does not take part in the reaction can be used as the solvent. Preferable examples of the solvent include benzene and toluene. The reaction temperature ranges from room temperature to a temperature at which the solvent is refluxed. The addition of a small amount of ammonium acetate brings about a rapid progress of the reaction.

Then, the schiff base (XVI) thus obtained is reduced to an amine compound (XVII). Examples of the reducing agent used include lithium aluminum hydride, sodium borohydride, and sodium cyanoborohydride. Further, it is possible to conduct catalytic reduction in the presence of a catalyst comprising palladium-carbon, platinum oxide, Raney nickel, or the like. Any solvent which does not take part in the reaction may be used as the solvent for the reaction. The reaction temperature ranges from 0° C. to a temperature at which the solvent is refluxed. Preferable examples of the solvent for the reaction include tetrahydrofuran and diethyl ether when aluminum hydride is used; methanol, ethanol, and a mixed solvent comprising water and alcohol when sodium borohydride or cyanoborohydride is used; and ethyl acetate, methanol, and ethanol in the case of the catalytic reduction.

Process 6 (production via isobromide)

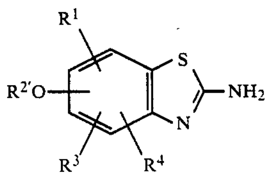

(XIV)

-continued

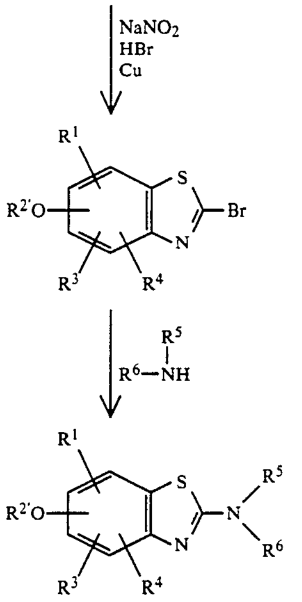

(XVIII)

(XIX)

(XX)

wherein $R^1$, $R^{2'}$, $R^3$, $R^4$, $R^5$, and $R^6$ are as defined above.

A compound (XIV) having an amino group is diazotized according to the method described in Organic Synthesis, Collective Volume I, p.135 and decomposing the formed diazonium salt to prepare an iminobromo compound (XVIII). Example of the diazotizing agent include sodium nitrite and hydrobromic acid. Further, hydrobromic acid and copper are used in the decomposition of the diazonium salt. Any solvent which does not take part in the reaction can be used as the solvent, and hydrobromic acid is also used as the solvent. The reaction temperature ranges from 0° C. to a temperature at which the solvent is refluxed.

The iminobromo compound (XVIII) is reacted with an amine in the presence of a base to prepare a compound (XX). Any base may be used as the base, and any solvent which does not take part in the reaction may be used as the solvent. Further, the reaction may be conducted in the absence of any solvent. The reaction temperature ranges from room temperature to 180° C.

Process 7 (reduction of amide compound to amine compound)

When $R^6$ in the general formula (I) is a group represented by the formula $—CH_2—J$, wherein J is as defined above, the compound of the present invention can be prepared also by the following process:

(XIII)

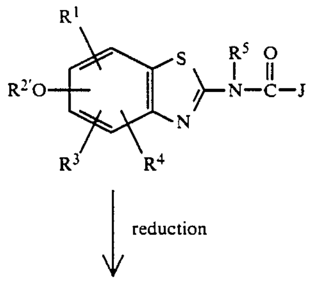

-continued (XXI)

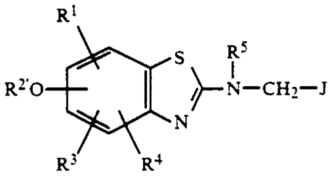

wherein $R^1$, $R^{2'}$, $R^3$, $R^4$, $R^5$, and J are as defined above.

The amide (XIII) is reduced into an amine compound (XXI). Lithium aluminum hydride and diborane are used as the reducing agent. Any solvent which does not take part in the reaction may be used as the solvent for the reaction. Preferable examples of the solvent include tetrahydrofuran and diethyl ether. The reaction temperature ranges from room temperature to a temperature at which the solvent is refluxed.

When $R^{2'}$ is an acyl group or a group represented by the formula

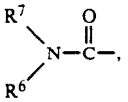

wherein $R^7$ and $R^8$ are as defined above, diborane is used, while when $R^{2'}$ is any other group, lithium aluminum hydride is used.

Process 8 (demethylation)

When $R^2$ in the general formula (I) is H, the compound of the present invention can be prepared also by the following process:

(XXII)

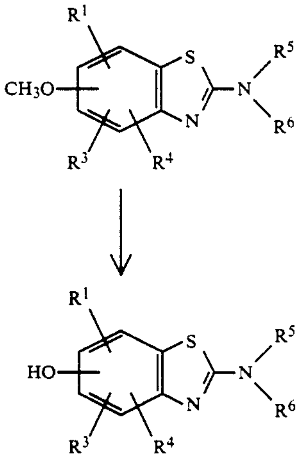

(XXIII)

wherein $R^1$, $R^3$, $R^4$, $R^5$, and $R^6$ are as defined above.

A methyl compound (XXII) is demethylated into a demethylated compound (XXIII). Examples of the demethylating agent used include boron tribromide, trimethylsilyl iodide, and hydrogen bromide/acetic acid. Any solvent which does not take part in the reaction can be used as the solvent. Methylene chloride, chloroform, etc. are particularly preferable. The reaction temperature ranges from 0° C. to a temperature at which the solvent is refluxed.

As described above, when $R^2$ is H, the reaction is usually conducted by making use of a starting material comprising a compound in which the hydroxyl group is protected in the form of a methyl ether, and the demethylation is conducted in the final step of preparing each object compound, thereby obtaining each object compound.

For easy understanding, a specific example will now be given.

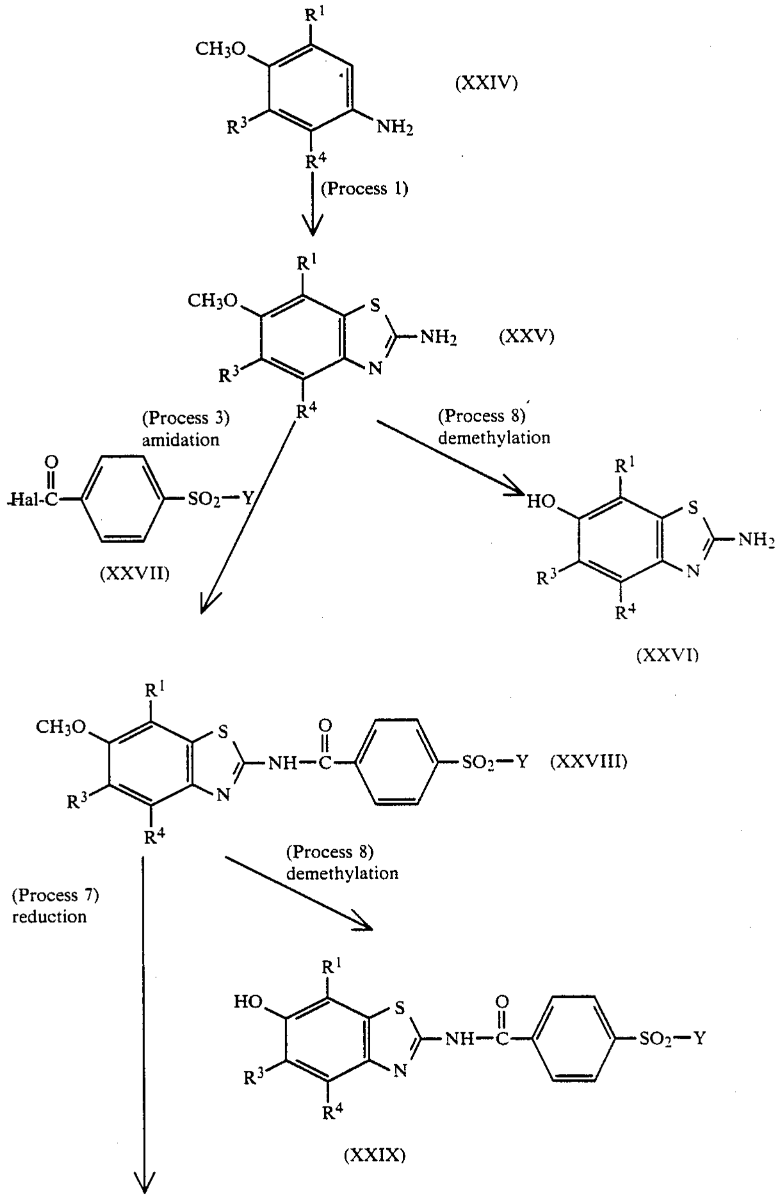

-continued

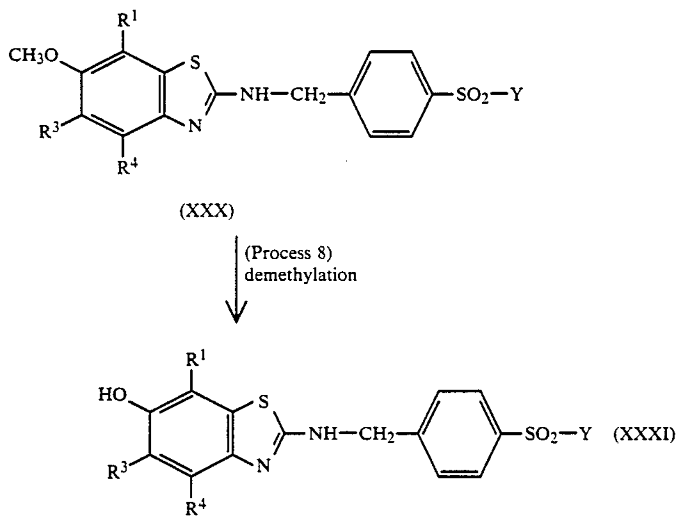

wherein $R^1$, $R^3$, $R^4$, and Y are as defined above and Hal is a halogen atom.

The effect of the present invention will now be described in more detail with reference to the following examples of pharmacological experiment.

EXAMPLES OF PHARMACOLOGICAL EXPERIMENT

Effect on generation of leukotriene $C_4$ (LT) from sliced lung of guinea pig

Experimental method

An antiovalbumin guinea pig serum (1/10 dilution; 0.5 ml/100 g) was intravenously injected into a male Hartley guinea pig (300–350 g) for passive sensitization. 16 to 18 hr after the passive sensitization, the blood was removed by circulation of the Tyrode solution and the lung was extirpated. The extirpated lung was cut into small pieces having a size of 1 mm×1 mm×1 mm while cooling the lung with ice. The pieces were washed, and 150 mg of the pieces was suspended on 1.8 ml of the Tyrode solution, followed by incubation at 37° C. for 5 min. A 3 μM test compound (the compound of the present invention) solution was added thereto, followed by incubation for 10 min. An antigen solution (ovalbumin; a final concentration of 10 μg/ml) was added thereto, followed by incubation for additional 15 min. The mixture was filtered through a nylon mesh. 100 μl of the filtrate was subjected to determination of the amount of leukotriene $C_4$ ($LTC_4$) with an RzA kit.

EXPERIMENTAL RESULTS

The percentage leukotriene $C_4$ ($LTC_4$) liberation inhibition of each compound (indicated by compound No. used in the Examples which will be described later) is shown in Table 1.

The compound No. in Table 1 corresponds to the compound No. in the Examples.

TABLE 1

| Compd. No. | Percentage inhibition 3 μM (%) | Compd. No. | Percentage inhibition 3 μM (%) |
|---|---|---|---|
| 8 | 75 | 33 | 46 |
| 9 | 36 | 34 | 70 |
| 10 | 78 | 35 | 68 |
| 13 | 35 | 37 | 39 |
| 17 | 35 | 40 | 32 |
| 19 | 36 | 51 | 56 |
| 20 | 33 | 52 | 62 |
| 21 | 48 | 53 | 69 |
| 22 | 61 | 54 | 58 |
| 24 | 95 | 57 | 42 |
| 25 | 36 | 58 | 64 |
| 26 | 85 | 59 | 71 |
| 28 | 34 | 60 | 36 |
| 29 | 43 | 61 | 36 |
| 30 | 79 | 64 | 32 |
| 31 | 62 | 68 | 70 |
| 32 | 44 | 69 | 42 |
| 70 | 30 | 103 | 48 |
| 71 | 53 | 106 | 49 |
| 75 | 50 | 108 | 30 |
| 76 | 72 | 110 | 41 |
| 86 | 31 | 113 | 49 |
| 87 | 32 | 115 | 39 |
| 88 | 79 | 117 | 51 |
| 90 | 41 | 122 | 34 |
| 91 | 53 | 123 | 71 |
| 92 | 64 | 124 | 72 |
| 93 | 83 | 126 | 66 |
| 94 | 79 | 128 | 60 |
| 95 | 72 | 134 | 88 |
| 96 | 77 | 135 | 41 |
| 98 | 60 | 136 | 67 |
| 99 | 43 | 137 | 40 |
| 101 | 37 | 141 | 53 |

From the above results of the pharmacological experiment, it is apparent that the compound of the present invention inhibits the production of leukotriene. Therefore, the compound of the present invention is useful as a pharmaceutical based on the leukotriene production inhibitory action. The compound of the present invention is effective against allergy, especially asthma, and other diseases which are considered to be caused by leukotrines, e.g., affections of the skin, such as psoriasis and eczema, allergic rhinitis, and affection of a cardiovascular system.

Further, various experiments conducted by the present inventors have revealed that the compound of the present invention can suppress the production of leukotriene due to 5-lipoxygenase inhibition and further exhibits its effect in oral administration in the case of an asthma model. Therefore, the compound of the present invention is particularly useful as a therapeutic and preventive agent and therefore invaluable.

Further, the compound of the present invention has a low toxicity and a high safety and is therefore useful also from these viewpoints.

Specifically, with respect to the safety, all of the compounds of the present invention exhibited no serious toxicity in a single oral administration (300 mg/kg) to a guinea pig (Hartley; a weight of 300–350 g).

Therefore, the compound of the present invention is useful as a therapeutic composition for inhibiting the leukotriene production due to 5-lipoxygenase inhibition.

Specifically, the compound of the present invention is useful as therapeutic and preventive agents for diseases which are considered to be caused by leukotrienes, e.g., affection of the skin, such as psoriasis and eczema, and allergic diseases such as allergic rhinitis and asthma. The compound of the present invention is particularly useful as an antiasthmatic agent.

The compound of the present invention is administered as a therapeutic and preventive agent for these diseases in the form of tablets, powders, granules, capsules, medicated syrups, or inhalations. The dose of the compound of the present invention will remarkably vary depending upon the symptom, age, kind of the diseases, etc. In general, the compound may be administered in a dose of about 0.1 to 1000 mg, preferably 1 to 500 mg per adult per day in one to several portions.

Pharmaceutical preparations are prepared from the compound of the present invention by making use of a commonly accepted carrier for pharmaceutical preparations according to an ordinary method.

Specifically, when a solid preparation for oral administration is prepared, the effective ingredient is blended with a vehicle and, if necessary, a binder, a disintegrator, a lubricant, a colorant, a corrigent, etc., followed by preparation of tablets, coated tablets, granules, powders, and capsules.

Examples of the vehicle include lactose, corn starch, sucrose, glucose, sorbitol, crystalline cellulose, and silicon dioxide. Examples of the binder include polyvinyl alcohol, polyvinyl ether, ethylcellulose, methylcellulose, acacia, tragacanth, gelatin, shellac, hydroxypropylcellulose, hydroxypropylmethylcellulose, calcium citrate, dextrin, and pectin. Examples of the lubricant include magnesium stearate, talc, polyethylene glycol, silica, and hydrogenated vegetable oil. Any colorant of which the addition to pharmaceuticals is officially allowed can be used as the colorant. Examples of the corrigent include cacao powder, menthol, aromatic powder, mentha powder, borneol, and powdered cinnamon bark. It is a matter of course that a sugar coating, a gelatin coating and, if necessary, suitable other coatings may be applied on these tablets and granules.

When parenteral preparations are prepared, a pH modifier, a buffering agent, a stabilizer, a solubilizing agent, etc. are added to the effective ingredient, followed by preparation of parenteral preparations for subcutaneous injection, intramuscular injection, and intravenous injection according to an ordinary method.

Examples of the present invention will now be described. It is needless to say that the invention of the present invention is not limited to these only.

Although the following Examples also include starting materials, the object compounds have each a compound No. attached thereto.

Further, in the column of $^1H$—NMR of Tables 2 to 12, the signals of active hydrogen which can be replaced with $D_2O$ were omitted.

EXAMPLE 1

2-Amino-6-methoxy-4,5,7-trimethylbenzothiazole

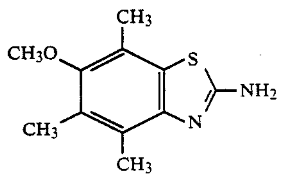

100 g of 1-amino-4-methoxy-2,3,5-trimethylbenzene was dissolved in 1000 ml of acetic acid and 50 ml of water. 212 g of potassium thiocyanate was added at room temperature to the resulting solution. The reaction mixture was cooled with ice, and 37.5 ml of bromine was dropwise added thereto, followed by stirring for 30 min. An aqueous 1N sodium hydroxide solution was added thereto to neutralize the reaction mixture. The resulting insoluble matter was separated by filtration and washed with water. The solid was recrystallized from methanol/tetrahydrofuran, thereby preparing 123 g of the title compound.

$^1H$—NMR ($DMSO$—$d_6$) δ: 2.16(3H, s), 2.24(3H, s), 2.35(3H, s), 3.59(3H, s)

EXAMPLE 2

The same procedures as those described in Example 1 were repeated to prepare compounds shown in Table 2.

TABLE 2

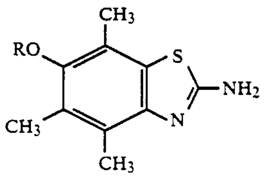

| Compd. No. | R | m.p. (°C.) | $^1$H-NMR |
|---|---|---|---|
| 1 | 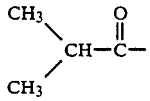 | 186~190 | ($CDCl_3$—$CD_3OD$) δ; 1.24(6H, d, J=8Hz), 1.92(3H, s), 2.04(3H, s), 2.32(3H, s), 2.5~2.9(1H, m) |
| 2 | 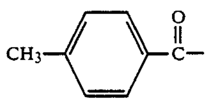 | 274~278 | (DMSO-$d_6$) δ; 2.00(3H, s), 2.08(3H, s), 2.38(3H, s), 2.40 (3H, s), 7.36(2H, d, J=8Hz), 8.04(2H, d, J=8Hz) |
| 3 | 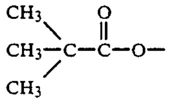 | 248~252 | (DMSO-$d_6$) δ; 1.37(9H, s), 2.00(3H, s), 2.07(3H, s), 2.39 (3H, s) |
| 4 | 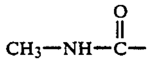 | 247~250 | (DMSO-$d_6$) δ; 2.04(3H, s), 2.16(3H, s), 2.39(3H, s), 2.70 (3H, d, J=4.5Hz) |
| 5 | 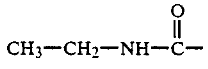 | 247~251 | (DMSO-$d_6$) δ; 1.10(3H, t, J=7Hz), 2.07(3H, s), 2.12(3H, s), 2.36(3H, s), 3.10(2H, m) |
| 6 | 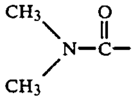 | 240~242 | (DMSO-$d_6$) δ; 2.01(3H, s), 2.13(3H, s), 2.33(3H, s), 2.88 (3H, s), 3.04(3H, s) |
| 7 | 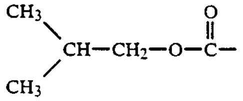 | 150~151 | (DMSO-$d_6$) δ; 0.97(6H, d, J=8Hz), 2.04(3H, s), 1.8~2.2 (1H, m), 2.13(3H, s), 2.36(3H, s), 4.00(2H, d) |

EXAMPLE 3

2-Amino-6-hydroxy-4,5,7-trimethylbenzothiazole

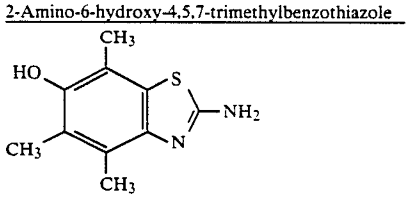

5 g of 2-amino-6-methoxy-4,5,7-trimethylbenzothiazole prepared in Example 1 was suspended in 100 ml of methylene chloride. 50 ml of a methylene chloride solution of boron tribromide (1M) was added to the suspension, followed by heating under reflux for 30 min. The reaction mixture was poured into ice/water, and an aqueous sodium bicarbonate solution was added thereto for neutralization. The resulting crystal was separated by filtration and recrystallized from tetrahydrofuran/-methanol, thereby preparing 4.0 g of the title compound (white crystal).

m.p. (°C.): 268~272 (hydrochloride)

$^1$H—NMR (DMSO—$d_6$) (hydrochloride) δ: 2.16 (3H, s), 2.22 (3H, s), 2.32 (3H, s)

EXAMPLE 4

Compounds shown in Table 3 were prepared by conducting the procedures described in Example 3 subsequent to the procedures described in Example 1.

TABLE 3

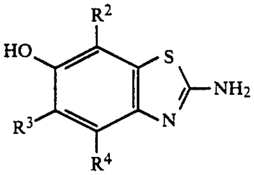

| Compd. No. | $R^2$ | $R^3$ | $R^4$ | Salt | m.p. (°C.) | $^1$H-NMR |
|---|---|---|---|---|---|---|
| 8 | $CH_3$— | $CH_3$— | $CH_3$— | hydrochloride | 268~272 | (DMSO-6) δ; 2.16(3H, s), 2.22(3H, s), 2.32(3H, s) |
| 9 | 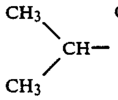 | $CH_3$— | $CH_3$— | hydrochloride | .225~227 | (DMSO-$d_6$) δ; 1.24(6H, d, J=8Hz), 2.13(3H, s), 2.30(3H, s), 3.30(1H, m) |
| 10 | 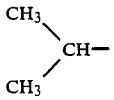 | 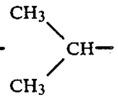 | H | hydrochloride | 200~202 | (DMSO-$d_6$) δ; 1.17(6H, d, J=8Hz), 2.08(6H, d, J=8Hz), 3.1~3.6(2H, m), 7.15(1H, s) |
| 11 | 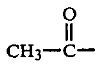 | $CH_3$— | $CH_3$— | free | 255~258 (dec.) | (DMSO-$d_6$) δ; 2.20(3H, s), 2.47(3H, s), 2.71(3H, s) |
| 12 | Cl | Cl | H | hydrochloride | 215~219 (dec.) | (DMSO-$d_6$) δ; 7.50(1H, s) |
| 13 | Br | Br | H | hydrochloride | 210~214 | (DMSO-$d_6$) δ; 7.50(1H, s) |
| 14 | 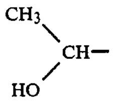 | $CH_3$— | $CH_3$— | free | 232~235 | (DMSO-$d_6$) δ; 1.31(3H, d, J=8Hz), 2.13(3H, s), 2.35(3H, s), 5.05(1H, m) |
| 15 | 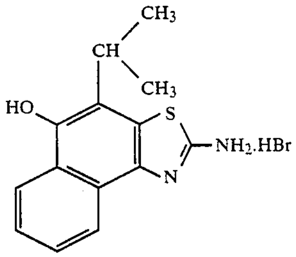 | | | | >300 (dec.) | (DMSO-$d_6$) δ; 1.38(6H, d, J=8Hz), 3.6(1H, m), 7.4~7.7(2H, m), 8.2~8.4(2H, m) |
| 16 | 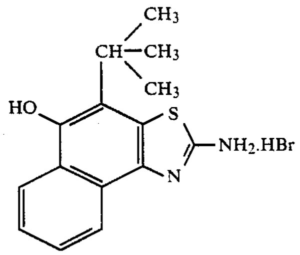 | | | | 265~270 | ($CDCl_3$—$CO_3OD$) δ; 1.73(9H, s), 7.4~7.8(2H, m), 7.9~8.3(2H, m) |
| 17 | 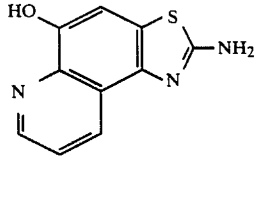 | | | free | 208~210 | (DMSO-$d_6$) δ; 7.47(1H, s), 7.60(1H, dd, J=10Hz, 6Hz), 8.66 (1H, dd, J=10Hz, 2.5Hz), 8.84(1H, dd, J=6Hz, 2.5 Hz) |

TABLE 3-continued

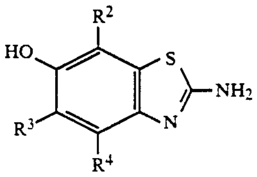

| Compd. No. | $R^2$ | $R^3$ | $R^4$ | Salt | m.p. (°C.) | $^1$H-NMR |
|---|---|---|---|---|---|---|
| 18 | | 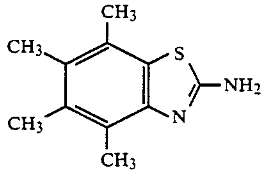 | | free | 120~122 | ($DMSO-d_6$) δ; 2.18(3H, s), 2.24(6H, s) |
| 19 | | 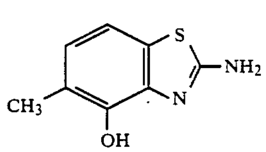 | | hydrochloride | 188~194 (dec.) | ($DMSO-d_6$) δ; 2.36(3H, s), 7.20(2H, s) |
| 20 | | 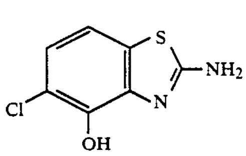 | | hydrochloride | 170~174 (dec.) | ($DMSO-d_6$) δ; 7.00(1H, d, J=10Hz), 7.20(1H, d, J=10Hz) |
| 21 | | 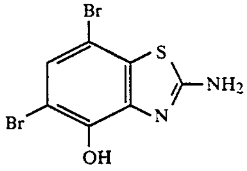 | | hydrochloride | 178~181 (dec.) | ($DMSO-d_6$) δ; 6.95(1H, s) |
| 22 | | 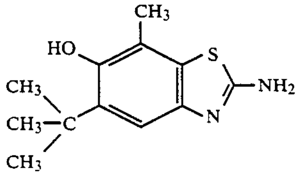 | | free | 182~186 | ($DMSO-d_6$) δ; 1.44(9H, s), 2.48(3H, s), 6.68(1H, s) |
| 23 | | 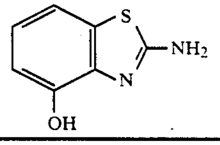 | | hydrochloride | 159~162 (dec.) | ($DMSO-d_6$) δ; 7.0~7.3(3H, m) |

EXAMPLE 5

6-Methoxy-2-(4-sulfamoylbenzamido)-4,5,7-trimethylbenzothiazole

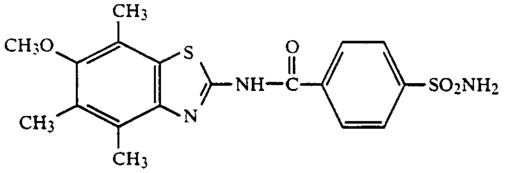

68 g of 4-sulfamoylbenzoic acid was suspended in 500 ml of dimethoxyethane. 50 ml of thionyl chloride was added to the suspension, followed by heating under reflux for 5 hr. Dimethoxyethane, thionyl chloride, and hydrogen chloride were distilled off in vacuo. The residue was dissolved in 500 ml of tetrahydrofuran. 50 g of 2-amino-6-methoxy-4,5,7-trimethylbenzothiazole (synthesized from 1-amino-4-methoxy-2,3,5-trimethylbenzene in the same manner as that described in Example 1) and 100 ml of pyridine were added to the resulting solution while cooling the solution with ice, followed by stirring at room temperature for 1 hr. The reaction mixture was poured into ice/water and then extracted with ethyl acetate under acidic conditions in the presence of hydrochloric acid. The organic phase was washed with water and then dried over anhydrous magnesium sulfate. The solvent was distilled off, and the residue was then recrystallized from methanol, thereby preparing 41.4 g of the title compound.

$^1H$—NMR (DMSO—$d_6$) δ: 2.24(3H, s), 2.38(3H, s), 2.52(3H, s), 3.63(3H, s), 7.49(2H, br, s), 7.89(2H, d, J=10 Hz), 8.20(2H, d, J=10 Hz), 12.83(1H, br, s)

EXAMPLE 6

6-Methoxy-2-(4-sulfamoylbenzylamino)-4,5,7-trimethylbenzothiazole

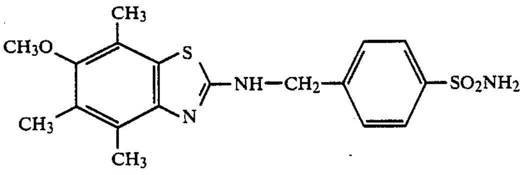

38.7 g of lithium aluminum hydride was suspended in 1.2 l of tetrahydrofuran. 41.4 of 6-methoxy-2-(4-sulfamoylbenzamido)-4,5,7-trimethylbenzothiazole was added at room temperature to the suspension while stirring. The mixture was heated under reflux for 40 min, and the reaction mixture was cooled with ice, followed by addition of water. The formed white precipitate was dissolved by addition of concentrated hydrochloric acid. An aqueous saturated sodium bicarbonate solution was added thereto to adjust the pH value to 4 to 5, followed by extraction with ethyl acetate. The organic phase was washed with water and dried over anhydrous magnesium sulfate, and the solvent was distilled off. The residue was recrystallized from acetone/methanol, thereby preparing 20.7 g of the title compound.

$^1H$—NMR (DMSO—$d_6$) δ: 2.14(3H, s), 2.22(3H, s), 2.34(3H, s), 3.56(3H, s), 4.58(2H, d, J=7), 7.23(2H, br, s), 7.47(2H, d, J=10), 7.72(2H, d, J=10), 8.32(1H, br, t, J=7)

EXAMPLE 7

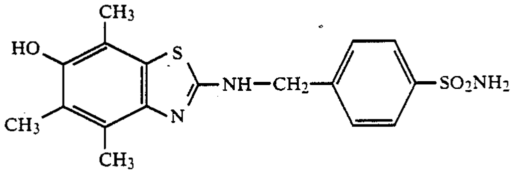

20.7 g of 6-methoxy-2-(4-sulfamoylbenzylamino)-4,5,7-trimethylbenzothiazole was suspended in 500 ml of methylene chloride. 200 ml of a methylene chloride solution of boron tribromide (1M) was added to the suspension while stirring at room temperature, followed by heating under reflux for 30 min. The reaction mixture was allowed to cool, poured into an aqueous saturated sodium bicarbonate solution for neutralization and then extracted with ethyl acetate. The organic phase was washed with water and dried over anhydrous magnesium sulfate. The solvent was distilled off, and the resulting crystal was separated by filtration, thereby preparing 19.5 g of the title compound.

$^1H$—NMR (DMSO—$d_6$) δ: 2.13(3H, s), 2.20(3H, s), 2.35(3H, s), 4.57(2H, d, J=7 Hz), 7.24(2H, br, s), 7.50(2H, d, J=9 Hz), 7.74(2H, d, J=9 Hz), 8.84(1H, br, s), 8.14(1H, br, t, J=7 Hz)

EXAMPLE 8

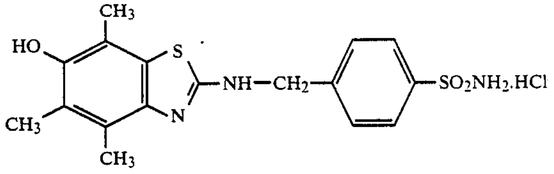

19.5 g of 6-hydroxy-2-(4-sulfamoylbenzylamino)-4,5,7-trimethylbenzothiazole was dissolved in 2 l of ethanol by heating. Ethanol containing hydrogen chloride dissolved therein was added thereto, followed by cooling. The formed crystal was separated by filtration, thereby preparing 19.5 g of the title compound in the form of a white crystal.

m.p. (°C.): 210 (dec.)

$^1H$—NMR (DMSO—$d_6$) δ: 2.15(3H, s), 2.20(3H, s), 2.38(3H, s), 4.84(2H, br, s), 7.56(2H, d, J=9 Hz), 7.78(2H, d, J=9 Hz)

EXAMPLE 9

The procedures described in Examples 1, 5, 6, and 7 were successively conducted to prepare compounds shown in Table 4.

TABLE 4

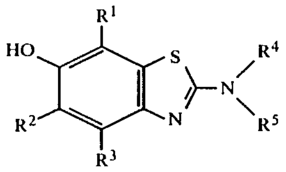

| Compd. No. | $R^1$ | $R^2$ | $R^3$ | $R^4$ | $R^5$ | Salt | m.p. (°C.) | $^1$H-NMR |
|---|---|---|---|---|---|---|---|---|
| 24 | $CH_3$— | $CH_3$— | $CH_3$— | H | 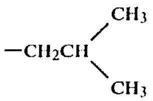 | hydrochloride | 222~226 | (DMSO-$d_6$) δ; 0.94(6H, d, J=10Hz), 2.00(1H, m), 2.14(3H, s), 2.21(3H, s), 2.36(3H, s), 3.13(2H, m) |
| 25 | $CH_3$— | $CH_3$— | $CH_3$— | H | 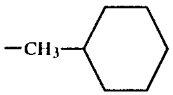 | hydrochloride | 140~142 | (DMSO-$d_6$) δ; 0.80~2.00(11H, m), 2.14(3H, s), 2.21(3H, s), 2.36(3H, s), 3.30(2H, m) |
| 26 | $CH_3$— | $CH_3$— | $CH_3$— | H | $-CH_2CH_3$ | hydrochloride | 216~213 | (DMSO-$d_6$) δ; 1.28(3H, t, J=8Hz), 2.19(3H, s), 2.26(3H, s), 2.40(3H, s), 3.57(2H, q, J=8Hz) |
| 27 | $CH_3$— | $CH_3$— | $CH_3$— | H | 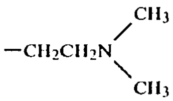 | free | deliquescent | (DMSO-$d_6$) δ; 2.11(3H, s), 2.18(9H, s), 2.33(3H, s), 2.43 (2H, t, J=7Hz), 3.32(2H, m) |
| 28 | $CH_3$— | $CH_3$— | $CH_3$— | H | 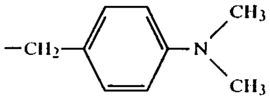 | hydrochloride | 145~147 | (DMSO-$d_6$) δ; 2.16(3H, s), 2.22(3H, s), 2.39(3H, s), 3.04 (6H, s), 4.73(2H, s), 7.53(4H, s) |
| 29 | $CH_3$— | $CH_3$— | $CH_3$— | H | 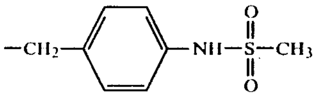 | hydrochloride | 154~157 | (DMSO-$d_6$) δ; 2.18(3H, s), 2.23(3H, s), 2.41(3H, s), 2.99 (3H, s), 4.73(2H, s), 7.23(2H, d, J=9Hz), 7.45 (2H, d, J=9Hz) |
| 30 | $CH_3$— | $CH_3$— | $CH_3$— | H | 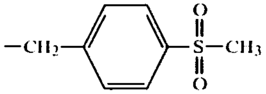 | free | 204~205 | (DMSO-$d_6$) δ; 2.10(3H, s), 2.16(3H, s), 2.33(3H, s), 3.16 (3H, s), 4.59(2H, d, J=8Hz), 7.60(2H, d, J=9Hz) 7.86(2H, d, J=9Hz) |

TABLE 4-continued

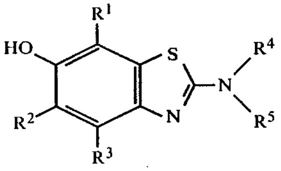

| Compd. No. | R¹ | R² | R³ | R⁴ | R⁵ | Salt | m.p. (°C.) | ¹H-NMR |
|---|---|---|---|---|---|---|---|---|
| 31 | $CH_3$— | $CH_3$— | $CH_3$— | H | 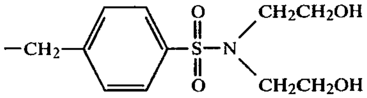 | hydrochloride | 222~225 | ($DMSO-d_6$) δ; 2.14(3H, s), 2.20(3H, s), 2.36(3H, s), 3.13 (4H, t, J=6Hz), 3.48(4H, t, J=6Hz), 4.80(2H, s), 7.56(2H, d, J=9Hz), 7.71(2H, d, J=9Hz) |
| 32 | $CH_3$— | $CH_3$— | $CH_3$— | H | 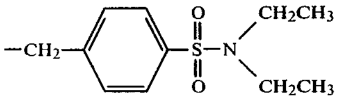 | free | 203~206 | ($CDCl_3$) δ; 1.09(6H, t, J=8Hz), 2.19(3H, s), 2.25(3H, s), 2.40(3H, s), 3.17(4H, q, J=8Hz), 4.56(2H, s), 7.36(2H, d, J=9Hz), 7.64(2H, d, J=9Hz) |
| 33 | $CH_3$— | $CH_3$— | $CH_3$— | H | 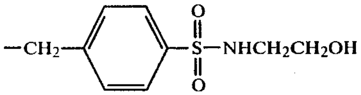 | free | 105~107 | ($DMSO-d_6$) δ; 2.14(3H, s), 2.18(3H, s), 2.36(3H, s), 2.78 (2H, t, J=7Hz), 3.33(2H, t, J=7Hz), 4.56(2H, d, J=6Hz), 7.50(2H, d, J=9Hz), 7.68(2H, d, J=9Hz) |
| 34 | $CH_3$— | $CH_3$— | $CH_3$— | H | 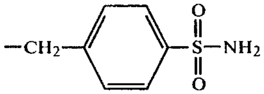 | hydrochloride | 210 (dec.) | ($DMSO-d_6$) δ; 2.15(3H, s), 2.20(3H, s), 2.38(3H, s), 4.84 (2H, s), 7.56(2H, d, J=9Hz), 7.78(2H, d, J=9Hz) |
| 35 | $CH_3$— | $CH_3$— | $CH_3$— | $-CH_2CH_3$ | 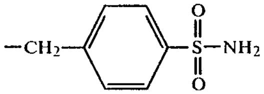 | hydrochloride | 135~138 | ($DMSO-d_6$) δ; 0.96(3H, t, J=8Hz), 2.16(3H, s), 2.21(3H, s), 2.39(3H, s), 2.76(2H, q, J=8Hz), 4.80(2H, s), 7.62(2H, d, J=10Hz), 7.81(2H, d, J=10Hz) |
| 36 | 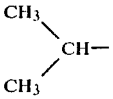 | 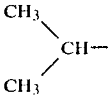 | H | H | 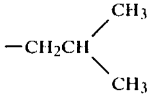 | hydrochloride | 198~200 | ($DMSO-d_6$) δ; 1.00(6H, d, J=8Hz), 1.18(6H, d, J=8Hz), 1.30 (6H, d, J=8Hz), 1.97(1H, m), 3.20~3.70(4H, m), 7.36(1H, s) |
| 37 | 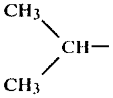 | 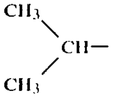 | H | H | 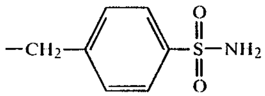 | hydrochloride | 170~172 | ($DMSO-d_6$) δ; 1.16(6H, d, J=8Hz), 1.28(6H, d, J=8Hz), 3.20~3.70(2H, m), 4.90(2H, s), 7.28(1H, s), 7.61 (2H, d, J=10Hz), 7.84(2H, d, J=10Hz) |

TABLE 4-continued

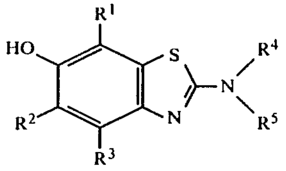

| Compd. No. | $R^1$ | $R^2$ | $R^3$ | $R^4$ | $R^5$ | Salt | m.p. (°C.) | $^1$H-NMR |
|---|---|---|---|---|---|---|---|---|
| 38 | 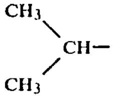 | 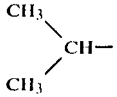 | H | H | 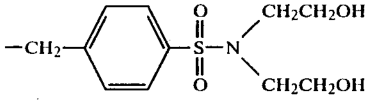 | free | 101~102 | ($DMSO-d_6$) δ; 1.12(6H, d, J=8Hz), 1.26(6H, d, J=8Hz), 3.10 (4H, t, J=6Hz), 3.30~3.60(6H, m), 4.58(2H, d, J=6Hz), 6.98(1H, s), 7.48(2H, d, J=10Hz), 7.70(2H, d, 10Hz) |
| 39 | 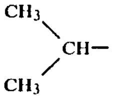 | 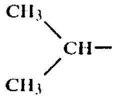 | H | H | 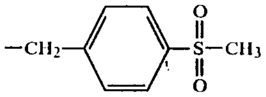 | free | 110~112 | ($DMSO-d_6$) δ; 1.14(6H, d, J=7Hz), 1.26(6H, d, J=7Hz), 2.96~3.64(2H, m), 3.18(3H, s), 4.64(2H, d, J=8Hz), 7.00(1H, s), 7.58(2H, d, J=10Hz), 7.88(2H, d, J=10Hz) |
| 40 | 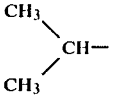 | 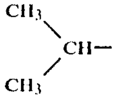 | H | $-CH_2CH_3$ | 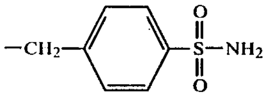 | free | 150~151 | ($DMSO-d_6$) δ; 0.98(3H, t, J=8Hz), 1.15(6H, d, J=7Hz), 1.28 (6H, d, J=7Hz), 2.76(2H, q, J=8Hz), 3.20~3.70 (2H, m), 4.60(2H, d, J=6Hz), 7.04(1H, s), 7.52 (2H, d, J=10Hz), 7.75(2H, d, J=10Hz) |
| 41 | H | H | H | H | 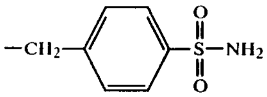 | free | 272~275 | ($DMSO-d_6$) δ; 4.76(2H, s), 6.70(1H, dd, J=10Hz, 3Hz), 7.06 (1H, d, J=3Hz), 7.20(1H, d, J=10Hz), 7.54(2H, d, J=10Hz), 7.81(2H, d, J=10Hz) |
| 42 | 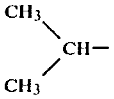 | $CH_3-$ | $CH_3-$ | H | 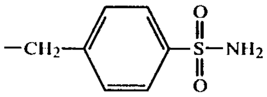 | hydrochloride | 168~170 | ($DMSO-d_6$) δ; 1.24(6H, d, J=7Hz), 2.13(3H, s), 2.36(3H, s), 3.30(1H, m), 4.76(2H, s), 7.50(2H, d, J=10Hz), 7.74(2H, d, J=10Hz) |
| 43 | $CH_3-$ | $CH_3-$ | H | H | 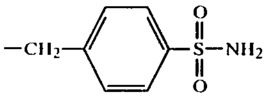 | hydrochloride | 195~198 | ($DMSO-d_6$) δ; 2.24(6H, s), 4.90(2H, s), 7.19(1H, s), 7.60 (2H, d, J=10Hz), 7.80(2H, d, J=10Hz) |
| 44 | $CH_3-$ | 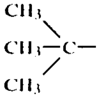 | H | H | 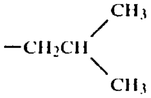 | hydrochloride | 95~100 | ($CDCl_3$) δ; 1.00(6H, d, J=7Hz), 1.22(9H, s), 2.24(3H, s), 2.60(1H, m), 3.04(2H, d, J=6Hz), 6.98(1H, s) |

TABLE 4-continued
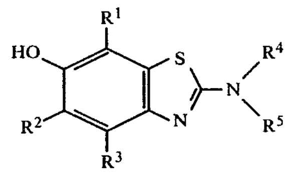
| Compd. No. | $R^1$ | $R^2$ | $R^3$ | $R^4$ | $R^5$ | Salt | m.p. (°C.) | $^1$H-NMR |
|---|---|---|---|---|---|---|---|---|
| 45 | | 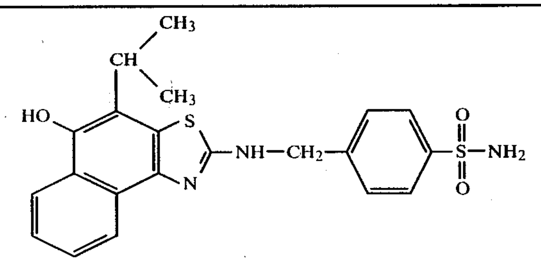 | | | | free | 232~234 (dec.) | (DMSO-$d_6$) δ; 1.34(6H, d, J=8Hz), 3.5~3.7(1H, m), 4.65 (2H, d, J=6Hz), 7.2~7.4(2H, m), 7.54(2H, d, J=10Hz), 7.75(2H, d, J=10Hz), 8.0~8.3(2H, m) |
| 46 | 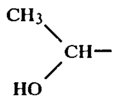 | $CH_3$— | $CH_3$— | H | 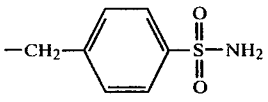 | free | 156~157 | (DMSO-$d_6$) δ; 1.28(3H, d, J=8Hz), 2.14(3H, s), 2.38(3H, s), 4.58(2H, d, J=8Hz), 5.08(1H, m), 7.48(2H, d, J=10Hz), 7.76(2H, d, J=10Hz) |
| 47 | 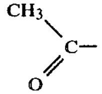 | $CH_3$— | $CH_3$— | H | 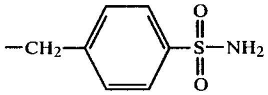 | free | 228~230 | (DMSO-$d_6$) δ; 2.22(3H, s), 2.50(3H, s), 2.72(3H, s), 4.68 (2H, d, J=8Hz), 7.63(2H, d, J=10Hz), 7.86(2H, d, J=10Hz) |
| 48 | | 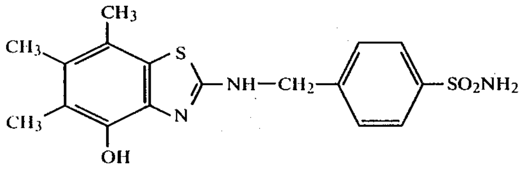 | | | | free | 229~230 | (DMSO-$d_6$) δ; 1.94(6H, s), 2.02(3H, s), 4.49(2H, d, J=7Hz), 7.32(2H, d, J=10Hz), 7.56(2H, d, J=10Hz) |
| 49 | $CH_3$— | 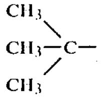 | H | H | 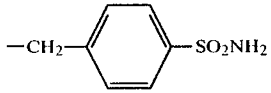 | hydrochloride | 218~220 | (DMSO-$d_6$) δ; 1.22(9H, s), 1.32(3H, s), 4.58(2H, s), 7.6~7.9(4H, m) |

EXAMPLE 10

The procedures described in Examples 1, 5, and 7 were successively conducted to prepare compounds shown in Table 5.

TABLE 5

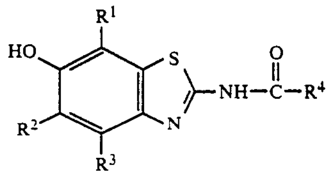

| Compd. No. | $R^1$ | $R^2$ | $R^3$ | $R^4$ | m.p. (°C.) | $^1$H-NMR |
|---|---|---|---|---|---|---|
| 50 | $CH_3$— | $CH_3$— | $CH_3$— | 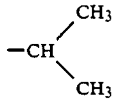 | 226~227 | ($CDCl_3$) δ; 1.28(6H, d, J=8Hz), 2.28(3H, s), 2.40(3H, s), 2.54(3H, s), 2.40~2.70(1H, m) |
| 51 | $CH_3$— | $CH_3$— | $CH_3$— | 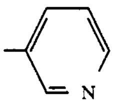 | 273~276 | (DMSO-$d_6$) δ; 2.20(3H, s), 2.37(3H, s), 2.51(3H, s), 7.50 (1H, dd, J=8Hz, 6Hz), 8.36(1H, m, J=8Hz), 8.70 (1H, dd, J=6Hz, 3Hz), 9.12(1H, d, J=3Hz) |
| 52 | $CH_3$— | $CH_3$— | $CH_3$— | 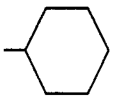 | 205~208 | (DMSO-$d_6$) δ; 2.21(3H, s), 2.36(3H, s), 2.52(3H, s), 1.10~2.40(11H, m) |
| 53 | $CH_3$— | $CH_3$— | $CH_3$— | $-CH_3$ | 230~232 | (DMSO-$d_6$) δ; 2.16(3H, s), 2.20(3H, s), 2.32(3H, s), 2.46 (3H, s) |
| 54 | $CH_3$— | $CH_3$— | $CH_3$— | 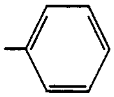 | 171~173 | (DMSO-$d_6$) δ; 2.22(3H, s), 2.36(3H, s), 2.52(3H, s), 7.40 7.70(3H, m), 8.00~8.20(2H, m) |
| 55 | $CH_3$— | $CH_3$— | $CH_3$— | 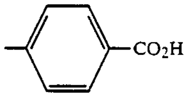 | >300 | (DMSO-$d_6$) δ; 2.24(3H, s), 2.36(3H, s), 2.52(3H, s), 8.06 (2H, d, J=9Hz), 8.24(2H, d, J=9Hz) |
| 56 | $CH_3$— | $CH_3$— | $CH_3$— | 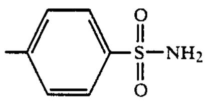 | >300 | (DMSO-$d_6$) δ; 2.24(3H, s), 2.36(3H, s), 2.52(3H, s), 7.96 (2H, d, J=10Hz), 8.27(2H, d, J=10Hz) |
| 57 | $CH_3$— | $CH_3$— | $CH_3$— | 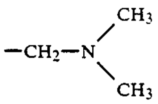 | 182~185 | ($CDCl_3$) δ; 2.29(3H, s), 2.38(6H, s), 2.42(3H, s), 2.57 (3H, s), 3.20(2H, s) |
| 58 | $CH_3$— | $CH_3$— | $CH_3$— | 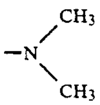 | 194~196 | (DMSO-$d_6$) δ; 2.16(3H, s), 2.26(3H, s), 2.42(3H, s), 2.93 (6H, s) |

TABLE 5-continued

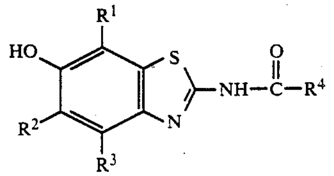

| Compd. No. | $R^1$ | $R^2$ | $R^3$ | $R^4$ | m.p. (°C.) | $^1$H-NMR |
|---|---|---|---|---|---|---|
| 59 | $CH_3$— | $CH_3$— | $CH_3$— | —$OCH_2CH_3$ | 155~156 | ($CDCl_3$) δ; 1.24(3H, t, J=8Hz), 2.26(3H, s), 2.39(3H, s), 2.52(3H, s), 4.26(2H, q, J=8Hz) |
| 60 | $CH_3$— | $CH_3$— | $CH_3$— | —$CO_2Et$ | 219~220 | (DMSO-$d_6$) δ; 1.28(3H, t, J=8Hz), 2.16(3H, s), 2.28(3H, s), 2.46(3H, s), 4.24(2H, q, J=8Hz) |
| 61 | $CH_3$— | $CH_3$— | $CH_3$— | —$CO_2H$ | 232~235 | (DMSO-$d_6$) δ; 2.16(3H, s), 2.29(3H, s), 2.44(3H, s) |
| 62 | $CH_3$— | $CH_3$— | $CH_3$— | —$CH_2CO_2Et$ | 240~241 | (DMSO-$d_6$) δ; 1.22(3H, t, J=8Hz), 2.19(3H, s), 2.30(3H, s), 2.45(3H, s), 3.57(2H, s), 4.09(2H, q, J=8Hz) |
| 63 | $CH_3$— | $CH_3$— | $CH_3$— | —$CH_2CO_2H$ | >300 | (DMSO-$d_6$) δ; 2.21(3H, s), 2.32(3H, s), 2.48(3H, s), 3.50 (2H, s) |
| 64 | $CH_3$— | $CH_3$— | $CH_3$— | —$CH_2CH_2CO_2Et$ | 209~210 | ($CDCl_3$) δ; 1.26(3H, t, J=8Hz), 2.29(3H, s), 2.40(3H, s), 2.55(3H, s), 2.76(4H, s), 4.18(2H, q, J=8Hz) |
| 65 | $CH_3$— | $CH_3$— | $CH_3$— | —$CH_2CH_2CO_2H$ | 242~245 | (DMSO-$d_6$) δ; 2.16(3H, s), 2.27(3H, s), 2.42(3H, s), 2.40~2.68(4H, m) |
| 66 | $CH_3$— | $CH_3$— | $CH_3$— | —$CH_2CH_2CH_2CO_2Et$ | 177~178 | ($CDCl_3$) δ; 1.26(3H, t, J=8Hz), 1.98~2.24(2H, m), 2.20~2.60(4H, m), 2.30(3H, s), 2.42(3H, s), 2.56 (3H, s), 4.14(2H, q, J=8Hz) |
| 67 | $CH_3$— | $CH_3$— | $CH_3$— | —$CH_2CH_2CH_2CO_2H$ | 260~263 | (DMSO-$d_6$) δ; 1.74~2.02(2H, m), 2.21(3H, s), 2.20~2.60 (4H, m), 2.32(3H, s), 2.48(3H, s) |
| 68 | 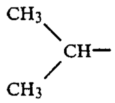 | 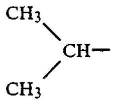 | H | 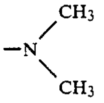 | 123~125 | (DMSO-$d_6$) δ; 1.24(6H, d, J=7Hz), 1.41(6H, d, J=7Hz), 3.00 (6H, s), 3.1~3.7(2H, m), 7.26(1H, s) |

EXAMPLE 11

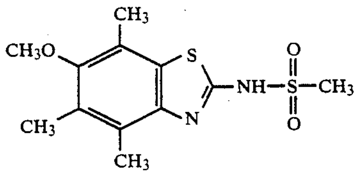

1.0 g of 2-amino-6-methoxy-4,5,7-trimethylbenzothiazole prepared in the same manner as that of Example 1 was dissolved in 50 ml of tetrahydrofuran. 2.5 g of potassium tert-butoxide was added to the resulting solution, followed by stirring at room temperature for 30 min. 3.5 ml of methanesulfonyl chloride was added thereto. The mixture was stirred at room temperature for 1 hr. The reaction mixture was poured into ice/water, followed by extraction with ethyl acetate. The organic phase was washed with water and dried over anhydrous magnesium sulfate. Then the solvent was distilled off in vacuo. The residue was purified by silica gel column chromatography, thereby preparing 600 mg of the title compound.

$^1$H—NMR ($CDCl_3$) δ: 2.26(3H, s), 2.30(6H, s), 3.40(3H, s), 3.68(3H, s)

EXAMPLE 12

Compounds shown in Table 6 were prepared by conducting the procedures described in Example 7 subsequent to the procedures described in Example 11.

TABLE 6

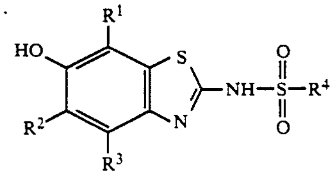

| Compd. No. | $R^1$ | $R^2$ | $R^3$ | $R^4$ | m.p. (°C.) | $^1$H-NMR |
|---|---|---|---|---|---|---|
| 69 | $CH_3$— | $CH_3$— | $CH_3$— | —$CH_3$ | 238~241 | (DMSO-$d_6$) δ; 2.15(3H, s), 2.22(3H, s), 2.29(3H, s), 2.97 (3H, s) |
| 70 | $CH_3$— | $CH_3$— | $CH_3$— | 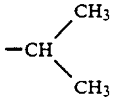 | 233~235 | (DMSO-$d_6$) δ; 1.26(6H, d, J=7Hz), 2.16(3H, s), 2.21(3H, s), 2.29(3H, s), 3.14(1H, m) |
| 71 | $CH_3$— | $CH_3$— | $CH_3$— | 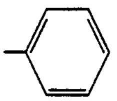 | 197~198 | ($CDCl_3$) δ; 2.19(3H, s), 2.23(6H, s), 7.26~7.52(3H, m), 7.97(2H, dd, J=4Hz) |
| 72 | 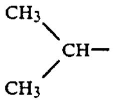 | 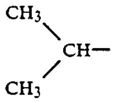 | H | —$CH_3$ | 269~271 | (DMSO-$d_6$) δ; 1.16(6H, d, J=7Hz), 1.30(6H, d, J=7Hz), 2.95 (3H, s), 3.16~3.60(2H, m), 6.92(1H, s) |
| 73 | $CH_3$— | $CH_3$— | $CH_3$— | 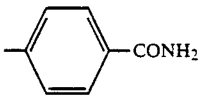 | >300 | (DMSO-$d_6$) δ; 2.13(3H, s), 2.23(3H, s), 2.26(3H, s), 7.93 (4H, s) |

EXAMPLE 13

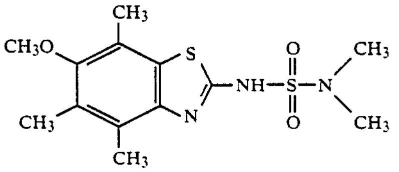

1.0 g of 2-amino-6-methoxy-4,5,7-trimethylbenzothiazole prepared in the same manner as that of Example 1 was dissolved in 50 ml of tetrahydrofuran. 0.8 g of sodium hydride (55%) and 2 ml of dimethylsulfamoyl chloride were added to the resulting solution, followed by heating under reflux for 1 hr. The reaction mixture was allowed to cool at room temperature and poured into ice/water, followed by extraction with ethyl acetate. The organic phase was washed with water and dried over anhydrous magnesium sulfate. Then the solvent was distilled off in vacuo. The residue was purified by silica gel column chromatography, thereby preparing 0.4 mg of the title compound.

$^1$H—NMR ($CDCl_3$) δ: 2.04(3H, s), 2.14(3H, s), 2.56(3H, s), 2.91(6H, s), 3.66(3H, s)

EXAMPLE 14

Compounds shown in Table 7 were prepared by conducting the procedures described in Example 7 subsequent to the procedures described in Example 13.

TABLE 7

| Compd. No. | | m.p. (°C.) | $^1$H-NMR |
|---|---|---|---|
| 74 | 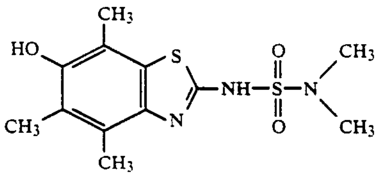 | 146~148 | (DMSO-$d_6$) δ; 2.16(3H, s), 2.21(3H, s), 2.30(3H, s), 2.68(6H, s) |

TABLE 7-continued

| Compd. No. | | m.p. (°C.) | $^1$H-NMR |
|---|---|---|---|
| 75 | 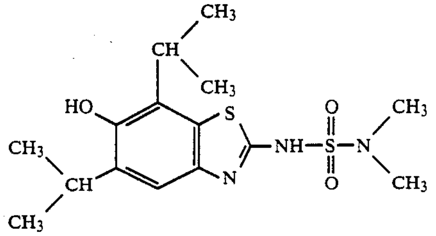 | 140~143 | (DMSO-$d_6$) δ; 1.26(6H, d, J=7Hz), 1.38(6H, d, J=7Hz), 3.00(3H, s), 3.04(3H, s), 3.0~3.6 (2H, m), 7.36(1H, s) |

EXAMPLE 15

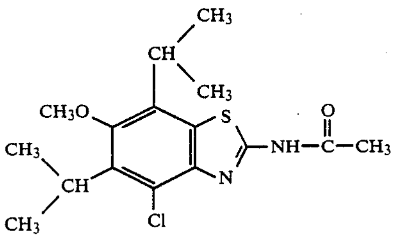

2.0 g of 2-acetamido-5,7-diisopropyl-6-methoxybenzothiazole synthesized by repeating the same procedures as those described in Example 5 subsequent to the procedures described in Example 1 was dissolved in 50 ml of benzene. 1 ml of sulfuryl chloride was added to the resulting solution, followed by stirring at room temperature for 1 hr. The reaction mixture was poured into ice/water, followed by extraction with ethyl acetate. The organic phase was washed with water and dried over anhydrous magnesium sulfate. Then the solvent was distilled off in vacuo. The residue was purified by silica gel column chromatography, thereby preparing 2.1 mg of the title compound in the form of an oleaginous substance.

$^1$H—NMR ($CDCl_3$) δ: 1.48(6H, d, J=7 Hz), 1.50(6H, d, J=7 Hz), 2.26(3H, s), 3.78(3H, s), 3.6~4.0(2H, m)

EXAMPLE 16

Compound No. 76

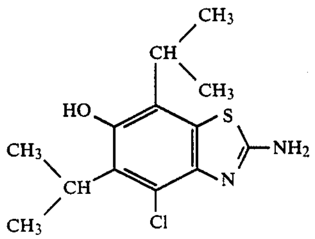

2.0 g of 2-acetamido-4-chloro-5,7-diisopropyl-6-methoxybenzothiazole prepared in the same manner as that of Example 15 was dissolved in 50 ml of methanol. 6 ml of an aqueous sodium hydroxide solution (5N) was added to the resulting solution, followed by heating under reflux for 1 hr. The reaction mixture was allowed to cool and water was added thereto, followed by extraction with ethyl acetate. The organic phase was washed with water and dried over anhydrous magnesium sulfate. Then the solvent was distilled off in vacuo. The residue was suspended in 50 ml of melthylene chloride, followed by the same procedures as those described in Example 7, thereby preparing 1.2 g of the title compound in the form of a white compound.

m.p. (°C.) 250~255 (dec.)

$^1$H—NMR (DMSO—$d_6$) δ: 1.24(6H, d, J=7 Hz), 1.34(6H, d, J=7 Hz), 3.3-3.8(2H, m)

EXAMPLE 17

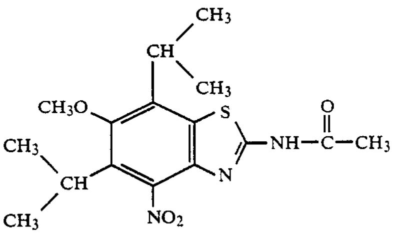

3.0 g of 2-acetamido-5,7-diisopropyl-6-methoxybenzothiazole synthesized by repeating the same procedures as those described in Example 5 subsequent to the procedures described in Example 1 was dissolved in 50 ml of acetic acid. 2 ml of concentrated nitric acid and a few drops of concentrated sulfuric acid were added to the resulting solution, followed by stirring at room temperature for 1 hr. Water was added to the reaction mixture, followed by extraction with ethyl acetate. The organic phase was washed with water and dried over anhydrous magnesium sulfate. Then the solvent was distilled off in vacuo. The residue was purified by silica gel column chromatography, thereby preparing 2.1 g of the title compound in the form of an oleaginous substance.

$^1$H—NMR ($CDCl_3$) δ: 1.32(6H, d, J=8 Hz), 1.40(6H, d, J=8 Hz), 2.35(3H, s), 3.2-3.8(2H, m), 3.78(3H, s)

EXAMPLE 18

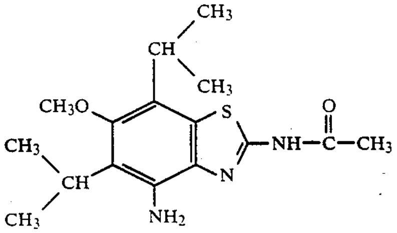

1.6 g of 2-acetamido-5,7-diisopropyl-6-methoxy-4-nitrobenzothiazole prepared in Example 17 was dissolved in 30 ml of methanol. A catalytic amount of a palladium-carbon powder (10%) was added to the resulting solution to conduct hydrogenation at 4 $kg/cm^2$. 1 hr after the initiation of the hydrogenation, the palladium-carbon powder was filtered off and methanol was distilled off in vacuo, thereby preparing 1.3 g of the title compound in the form of an oleaginous substance.

$^1H$—NMR ($CDCl_3$) δ: 1.37(6H, d, J=2 Hz), 1.45(6H, d, J=2 Hz), 2.23(3H, s), 3.4–3.8(2H, m), 3.73(3H, s)

EXAMPLE 19

Compound No. 77

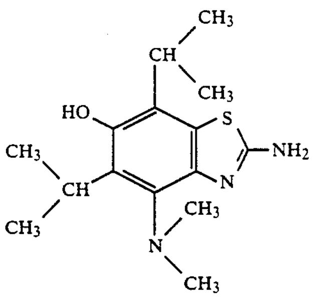

1.3 g of 2-acetamido-2-amino-5,7-diisopropyl-6-methoxybenzothiazole prepared in Example 18 was dissolved in 30 ml of acetonitrile. 0.4 g of sodium cyanoborohydride and 0.5 ml of an aqueous formaldehyde solution (37%) was added to the resulting solution, followed by stirring at room temperature for 1 hr. Water was added to the reaction mixture, followed by extraction with ethyl acetate. The organic phase was washed with water and dried over anhydrous magnesium sulfate. Then the solvent was distilled off in vacuo. The residue was treated in the same manner as that of Example 16, thereby preparing 0.9 g of the title compound in the form of a white crystal.

m.p. (°C.): 150～152

$^1H$—NMR ($CDCl_3$) δ: 1.20(6H, d, J=2 Hz), 1.48(6H, d, J=2 Hz), 2.93(6H, s), 3.2–4.2(2H, m)

EXAMPLE 20

Compound No. 77

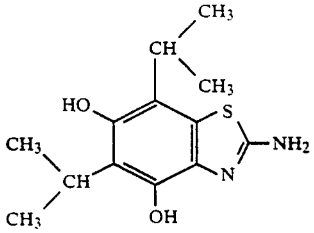

4.1 g of 2-acetamido-4-amino-5,7-diisopropyl-6-methoxybenzothiazole prepared in Example 18 was dissolved in 20 ml of concentrated hydrochloric acid. 1.5 g of sodium nitrite was added to the resulting solution, followed by stirring at room temperature for 30 min. 1 ml of concentrated sulfuric acid was added thereto, followed by stirring at room temperature for 30 min. Water was added to the reaction mixture, followed by extraction with ethyl acetate. The organic phase was washed with water and dried over anhydrous magnesium sulfate. Then the solvent was distilled off in vacuo. The residue was treated in the same manner as that of Example 16, thereby preparing 0.6 g of the title compound in the form of a white crystal.

m.p. (°C.): 254～257

$^1H$—NMR (DMSO—$d_6$) δ: 1.24(6H, d, J=8 Hz), 1.28(6H, d, J=8 Hz), 3.0–3.6(2H, m)

EXAMPLE 21

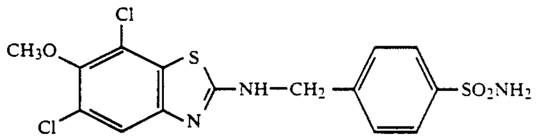

2.0 g of 5,7-dichloro-6-methoxy-2-(4-sulfamoylbenzamido)benzothiazole prepared in the same manner as that of Example 5 was dissolved in 50 ml of tetrahydrofuran. 15 ml of a tetrahydrofuran solution of diborane (1M) was added at room temperature to the resulting solution, followed by heating under reflux for 1 hr. The reaction mixture was allowed to cool. An aqueous ammonium chloride solution was added thereto, followed by extraction with ethyl acetate. The organic phase was washed with water and dried over anhydrous magnesium sulfate. Then the solvent was distilled off in vacuo. The residue was purified by silica gel column chromatography, thereby preparing 0.7 g of the title compound.

$^1H$—NMR (DMSO—$d_6$) δ: 3.82(3H, s), 4.67(2H, d, J=6 Hz), 7.48(1H, s), 7.52(2H, d, J=10 Hz), 7.82(2H, d, J=10 Hz)

EXAMPLE 22

Compounds shown in Table 8 were prepared in the same manner as that of Example 21.

TABLE 8

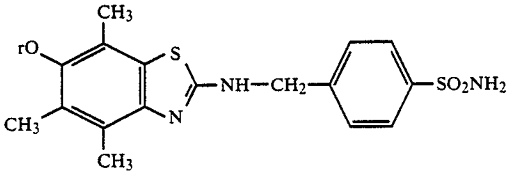

| Compd. No. | R | Salt | m.p. (°C.) | $^1$H-NMR |
|---|---|---|---|---|
| 79 | 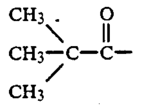 | free | 237~238 | (DMSO-$d_6$) δ; 1.52(9H, s), 1.96(3H, s), 2.04(3H, s), 2.34 (3H, s), 4.58(2H, d, J=6Hz), 7.46(2H, d, J=10Hz), 7.72(2H, d, J=10Hz) |
| 80 | 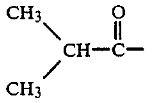 | free | 189~190 | (DMSO-$d_6$) δ; 1.30(6H, d, J=7Hz), 2.00(3H, s), 2.08(3H, s), 2.38(3H, s), 3.00(1H, m), 4.52(2H, d, J=6Hz), 7.50(2H, d, J=10Hz), 7.74(2H, d, J=10Hz) |
| 81 | 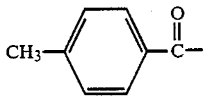 | free | 280~285 | (DMSO-$d_6$) δ; 2.06(3H, s), 2.12(3H, s), 2.44(6H, s), 4.62(2H, s), 7.27(2H, d, J=8Hz), 7.98(2H, d, J=8Hz), 7.42 (2H, d, J=10Hz), 7.74(2H, d, J=10Hz) |
| 82 | 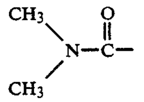 | hydrochloride | 223~226 | (DMSO-$d_6$) δ; 2.03(3H, s), 2.12(3H, s), 2.38(3H, s), 2.92(3H, s), 3.10(3H, s), 4.81(2H, s), 7.56(2H, d, J=10 Hz), 7.80(2H, d, J=10Hz) |
| 83 | 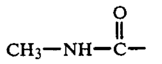 | free | 245~248 | (DMSO-$d_6$) δ; 2.01(3H, s), 2.08(3H, s), 2.34(3H, s), 2.63(3H, d, J=4.5Hz), 4.60(2H, d, J=6Hz), 7.46(2H, d, J=10 Hz), 7.70(2H, d, J=10Hz) |
| 84 | 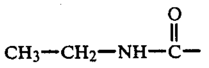 | free | 236~237 | (DMSO-$d_6$) δ; 1.08(3H, t, J=7Hz), 2.01(3H, s), 2.08(3H, s), 2.34(3H, s), 3.04(2H, m), 4.60(2H, d, J=6Hz), 7.44(2H, d, J=10Hz), 7.70(2H, d, J=10Hz) |

EXAMPLE 23

Compounds shown in Table 9 were prepared by conducting the procedures described in Example 7 subsequent to the procedures described in Example 21.

TABLE 9

| Compd. No. | | m.p. (°C.) | $^1$H-NMR |
|---|---|---|---|
| 85 | 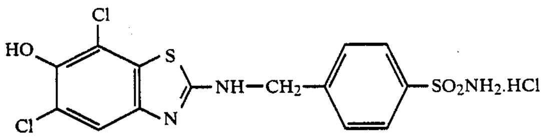 | 199~203 | (DMSO-$d_6$)δ; 4.68(2H, s), 7.36(1H, s), 7.56(2H, d, J=10Hz), 7.80(2H, d, J=10Hz) |
| 86 | 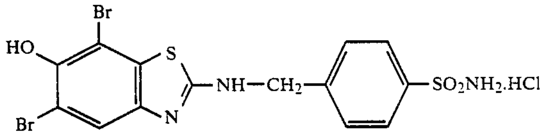 | 188~190 | (DMSO-$d_6$)δ; 4.64(2H, s), 7.44(2H, d, J=10Hz), 7.50(1H, s), 7.72(2H, d, J=10Hz) |
| 87 | 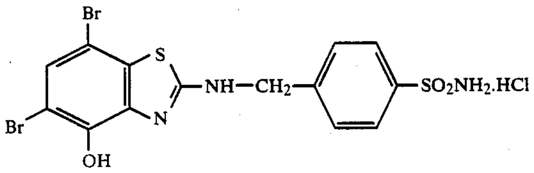 | 142~145 (dec.) | (DMSO-$d_6$)δ; 4.44(2H, s), 6.50(1H, s), 7.41(2H, d, J=10Hz), 7.73(2H, d, J=10Hz) |

TABLE 9-continued

| Compd. No. | | m.p. (°C.) | $^1$H-NMR |
|---|---|---|---|
| 88 | 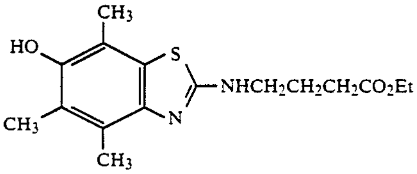 | 206~210 | (CDCl$_3$)δ; 1.20(3H, t, J=8Hz), 1.6~2.1(2H, m), 2.1~2.5 (2H, m), 2.20(3H, s), 2.26(3H, s), 2.44(3H, s), 3.36(2H, t, J=6Hz), 4.10(2H, q, J=8Hz) |
| 89 | 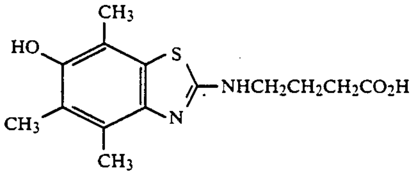 | 205~208 | (DMSO-d$_6$)δ; 1.6~2.0(2H, m), 2.0~2.4(2H, m), 2.16(3H, s), 2.20(3H, s), 2.34(3H, s), 2.7~4.0(2H, m) |

EXAMPLE 24

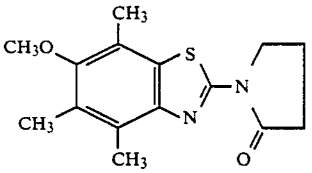

0.36 g of 2-(3-ethoxycarbonylpropylamino)-6-methoxy-4,5,7-trimethylbenzothiazole prepared in the same manner as that of Example 21 was dissolved in 5 ml of methanol, 6 ml of tetrahydrofuran, and 1 ml of water. 0.31 g of potassium hydroxide was added to the resulting solution, followed by stirring at 50° C. for 30 min. The solvent was distilled off in vacuo, and 20 ml of benzene and 2 ml of thionyl chloride were added to the residue. The reaction mixture was poured into ice/water, followed by extraction with ethyl acetate. The organic phase was washed with water and dried over anhydrous magnesium sulfate. Then the solvent was distilled off in vacuo. The residue was purified by silica gel column chromatography, thereby preparing 0.3 g of the title compound.

$^1$H—NMR (CDCl$_3$) δ: 2.0-2.4(2H, m), 2.30(3H, s), 2.43(3H, s), 2.56(3H, s), 2.5-2.9(2H, m), 3.68(3H, s), 4.20(2H, t, J=7 Hz)

EXAMPLE 25

Compound No. 90

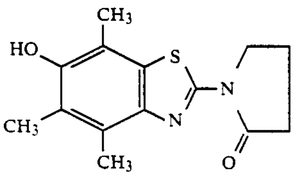

0.2 of the title compound in the form of a pale brown solid was prepared in the same manner as that of Example 7 by making use of 0.3 g of 6-methoxy-2-(2-oxopyrrolidino)-4,5,7-trimethylbenzothiazole prepared in Example 24 as the starting material.

m.p. (°C.): 215~220

$^1$H—NMR (DMSO—d$_6$) δ: 2.22(3H, s), 2.34(3H, s), 2.50(3H, s), 2.0-2.35(2H, m), 2.35-2.7(2H, m), 4.12(2H, t, J=6 Hz)

EXAMPLE 26

2-(3-Cyclohexylcarbamoylpropylamino)-6-methoxy-4,5,7-trimethylbenzothiazole

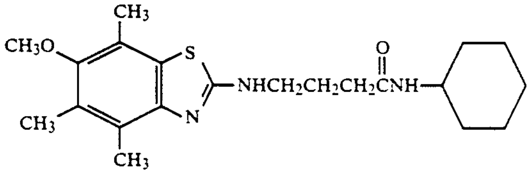

2.1 g of 2-(3-ethoxycarbonylpropylamino)-6-methoxy-4,5,7-trimethylbenzothiazole prepared in the same manner as that of Example 21 was dissolved in 6 ml of cyclohexylamine. The resulting solution was heated at 150° C. for 1 hr. Cyclohexylamine was distilled off, and the residue was purified by column chromatography, thereby preparing the title compound in the form of an oleaginous substance.

$^1$H—NMR (CDCl$_3$) δ: 0.8-2.2(12H, m), 2.26(3H, s), 2.34(3H, s), 2.48(3H, s), 2.2-2.9(3H, m), 3.42(2H, t, J=6 Hz), 3.70(3H, s)

EXAMPLE 27

Compound No. 91

2-(3-Cyclohexylcarbamoylpropylamino)-6-hydroxy-4,5,7-trimethylbenzothiazole

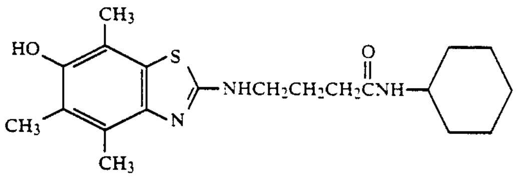

0.4 g of the title compound in the form of a white crystal was prepared in the same manner as that of Example 7 by making use of 0.5 g of 2-(3-cyclohexylcarbamoylpropylamino)-6-methoxy-4,5,7-trimethylbenzothiazole prepared in Example 26 as the starting material.

m.p. (°C.): 150~154

$^1$H—NMR (DMSO—$d_6$) δ: 1.0-2.1(12H, m), 2.14(3H, s), 2.20(3H, s), 2.34(3H, s), 2.1-2.5(3H, m), 3.44(2H, t, J=6 Hz)

EXAMPLE 28

2-Amino-6-hydroxy-4,5,7-trimethylbenzothiazole hydrochloride

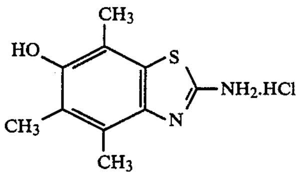

2 g of thiourea was dissolved in 50 ml of ethanol. 1.8 ml of concentrated hydrochloric acid and 6.7 g of 2,3,6-trimethyl-1,4-benzoquinone were added to the resulting solution, followed by stirring at room temperature for 2 hr. The resulting crystal was separated by filtration and then washed with acetonitrile, thereby preparing 2.5 g of the title compound in the form of a white crystal [preparation according to the method described in J. Org. Chem., 35, 4103 (1970)].

m.p. (°C.): 268~272 (dec.)

$^1$H—NMR (DMSO—$d_6$) δ: 2.16(3H, s), 2.22(3H, s), 2.32(3H, s)

EXAMPLE 29

Compounds shown in Table 10 were prepared in the same manner as that of Example 28.

TABLE 10

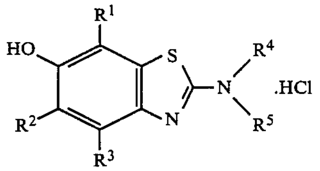

| Compd. No. | $R^1$ | $R^2$ | $R^3$ | $R^4$ | $R^5$ | m.p. (°C.) | $^1$H-NMR |
|---|---|---|---|---|---|---|---|
| 92 | $CH_3$— | $CH_3$— | $CH_3$— | H | H | 268~272 (dec.) | (DMSO-$d_6$) δ; 2.16(3H, s), 2.22(3H, s), 2.32(3H, s) |
| 93 | $CH_3$— | $CH_3$— | $CH_3$— | H | —$CH_3$ | 246~249 | ($CD_3OD$) δ; 2.23(3H, s), 2.24(3H, s), 2.39(3H, s), 3.18 (3H, s) |
| 94 | $CH_3$— | $CH_3$— | $CH_3$— | —$CH_3$ | —$CH_3$ | 230~233 | ($CD_3OD$) δ; 2.29(3H, s), 2.35(3H, s), 2.50(3H, s), 3.47 (6H, s) |
| 95 | $CH_3$— | $CH_3$— | $CH_3$— | H | —$CH_2CH_2CH_2CH_2CH_3$ | 181~183 | (DMSO-$d_6$) δ; 0.90(3H, t, J=8Hz), 1.20~1.75(6H, m), 2.16 (3H, s), 2.23(3H, s), 2.38(3H, s), 3.40~3.65 (2H, m) |
| 96 | $CH_3$— | $CH_3$— | $CH_3$— | H | 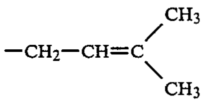 | 186~188 | (DMSO-$d_6$) δ; 1.72(6H, s), 2.14(3H, s), 2.22(3H, s), 2.36 (3H, s), 4.38(2H, d, J=7Hz), 5.22(1H, t, J=7Hz) |
| 97 | $CH_3$— | $CH_3$— | $CH_3$— | H | 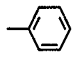 | 145~147 | (DMSO-$d_6$) δ; 2.22(3H, s), 2.30(3H, s), 2.52(3H, s), 7.2~8.2(5H, m) |
| 98 | $CH_3$— | $CH_3$— | $CH_3$— | H | 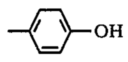 | 200~202 (dec.) | (DMSO-$d_6$) δ; 2.20(3H, s), 2.24(3H, s), 2.44(3H, s), 6.77 (2H, d, J=10Hz), 7.53(2H, d, J=10Hz) |
| 99 | $CH_3$— | $CH_3$— | $CH_3$— | H | 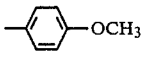 | 160~162 | (DMSO-$d_6$) δ; 2.28(3H, s), 2.32(3H, s), 2.56(3H, s), 3.84 (3H, s), 6.93(2H, d, J=10Hz), 7.42(2H, d, J=10 Hz |
| 100 | $CH_3$— | $CH_3$— | $CH_3$— | H | 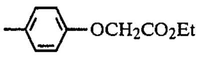 | 214~217 | (DMSO-$d_6$) δ; 1.24(3H, t, J=8Hz), 2.18(3H, s), 2.26(3H, s), 2.44(3H, s), 4.16(2H, q, J=8Hz), 4.70(2H, s), 6.90(2H, d, J=9Hz), 7.60(2H, d, J=9Hz) |
| 101 | $CH_3$— | $CH_3$— | $CH_3$— | H | 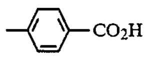 | 310~320 (dec.) | (DMSO-$d_6$) δ; 2.08(3H, s), 2.20(3H, s), 2.28(3H, s), 7.92 (4H, s) |
| 102 | $CH_3$— | $CH_3$— | $CH_3$— | H | 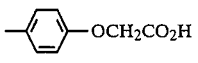 | 250~260 (dec.) | (DMSO-$d_6$) δ; 2.22(3H, s), 2.29(3H, s), 2.48(3H, s), 4.78 (2H, s), 6.98(2H, d, J=9Hz), 7.70(2H, d, J=9Hz) |
| 103 | $CH_3$— | $CH_3$— | $CH_3$— | H | 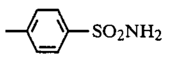 | 186~190 | (DMSO-$d_6$) δ; 2.20(3H, s), 2.30(3H, s), 2.50(3H, s), 7.70 (2H, d, J=9Hz), 7.90(2H, d, J=9Hz) |

TABLE 10-continued

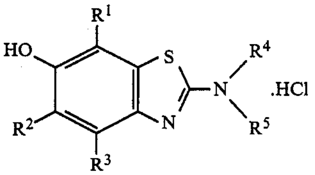

| Compd. No. | $R^1$ | $R^2$ | $R^3$ | $R^4$ | $R^5$ | m.p. (°C.) | $^1$H-NMR |
|---|---|---|---|---|---|---|---|
| 104 | $CH_3$— | $CH_3$— | $CH_3$— | H | 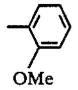 | 232~236 | ($CDCl_3$) δ; 2.18(3H, s), 2.24(3H, s), 2.44(3H, s), 3.84 (3H, s), 6.8~7.2(3H, m), 8.18(1H, m) |
| 105 | $CH_3$— | $CH_3$— | $CH_3$— | H | 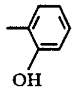 | 255~260 | (DMSO-$d_6$) δ; 2.18(3H, s), 2.24(3H, s), 2.40(3H, s), 6.5~7.1(3H, m), 7.7~7.9(1H, m) |
| 106 | $CH_3$— | $CH_3$— | $CH_3$— | H | 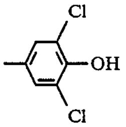 | 254~258 | (DMSO-$d_6$) δ; 2.18(3H, s), 2.24(3H, s), 2.48(3H, s), 7.52 (2H, s) |
| 107 | $CH_3$— | $CH_3$— | $CH_3$— | H | 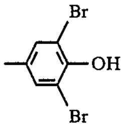 | 160~165 | (DMSO-$d_6$) δ; 2.24(3H, s), 2.30(3H, s), 2.50(3H, s), 8.12 (2H, s) |
| 108 | $CH_3$— | $CH_3$— | $CH_3$— | H | 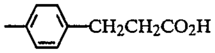 | 245~248 | (DMSO-$d_6$) δ; 2.16(3H, s), 2.25(3H, s), 2.46(3H, s), 2.4~2.6(2H, m), 2.6~2.9(2H, m), 7.10(2H, d, J=9 Hz), 7.60(2H, d, J=9Hz) |
| 109 | $CH_3$— | $CH_3$— | $CH_3$— | H | 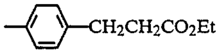 | 167~170 | (DMSO-$d_6$) δ; 1.16(3H, t, J=8Hz), 2.16(3H, s), 2.24(3H, s), 2.45(3H, s), 2.60(2H, t, J=6Hz), 2.76(2H, t, J=6Hz), 4.02(2H, q, J=8Hz), 7.16(2H, d, J=9Hz), 7.70(2H, d, J=9Hz) |
| 110 | $CH_3$— | $CH_3O$— | $CH_3O$— | H | H | 136~138 | (DMSO-$d_6$) δ; 2.16(3H, s), 3.76(3H, s), 3.87(3H, s) |

EXAMPLE 30

Compound No. 111

2-Amino-4-chloro-5-hydroxynaphtho[1,2-d]thiazole

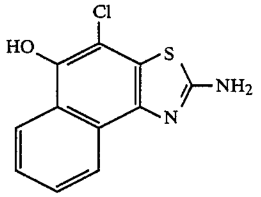

5 g of 2-amino-5-hydroxynaphtho[1,2-d]thiazole prepared in Example 28 [J. Org. Chem., 35, 4103(1970)] was suspended in 50 ml of acetic acid. A chlorine gas was blown into the suspension, followed by stirring at room temperature for 10 min. The crystal contained in the reaction mixture was separated by filtration, dissolved in ethyl acetate, washed with an aqueous saturated sodium bicarbonate solution, and dried over anhydrous magnesium sulfate. The solvent was distilled off in vacuo, and the residue was purified by silica gel chromatography, thereby preparing 2.0 g of the title compound in the form of a white crystal.

m.p. (°C.): >300

$^1$H—NMR (DMSO—$d_6$) δ: 7.22(2H, s), 7.4-7.7(2H, m), 8.2-8.4(2H, m), 8.90(1H, s)

EXAMPLE 31

The following compound was prepared in the same manner as that of Example 30.

Compound No. 112

2-Amino-4-bromo-5-hydroxynaphtho[1,2-d]thiazole

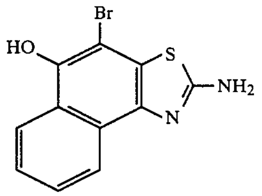

m.p. (°C.): >300

$^1H$—NMR (DMSO—$d_6$) δ: 7.10(2H, s), 7.3-7.6(2H, m), 8.0-8.3(2H, m), 8.75(1H, s)

EXAMPLE 32

2-Bromo-5,7-diisopropyl-6-methoxybenzothiazole

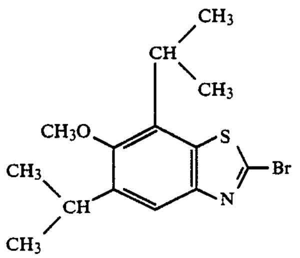

52 g of 2-amino-5,7-diisopropyl-6-methoxybenzothiazole (synthesized from 1-amino-3,5-diisopropyl-6-methoxybenzene according to the method described in Beilstein 27 (2), p.334) was dissolved in 700 ml of tetrahydrofuran. 58 ml of hydrobromic acid (47%) was added to the resulting solution while cooling the solution with ice, followed by addition of 18 g of sodium nitrite. The mixture was stirred for 1 hr, and 2.5 g of powdered copper was added thereto. The mixture was gradually heated and stirred at 50° C. for 1 hr. The reaction mixture was allowed to cool. Water was added thereto, followed by extraction with ethyl acetate. The organic phase was washed with water and dried over anhydrous magnesium sulfate. The solvent was distilled off in vacuo, and the residue was purified by silica gel chromatography, thereby preparing 32 g of the title compound in the form of an oleaginous substance.

$^1H$—NMR ($CDCl_3$) δ: 1.28(6H, d, J=7 Hz), 1.36(6H, d, J=7 Hz), 3.2-3.6(2H, m), 3.72(3H, s), 7.64(1H, s)

EXAMPLE 33

5,7-Diisopropyl-2-(ethoxycabonylphenylamino)-6-methoxybenzothiazole

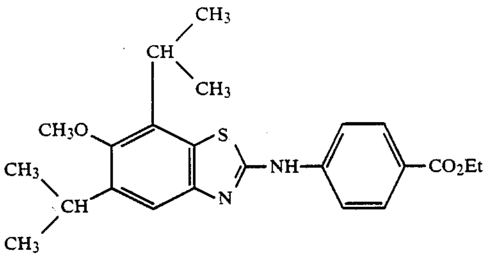

32 g of 2-bromo-5,7-diisopropyl-6-methoxybenzothiazole prepared in Example 32 was mixed with 50 g of 4-ethoxycarbonylaniline. The mixture was stirred at 100° C. for 30 min. The reaction mixture was allowed to cool at room temperature, and the solidified reaction product was dissolved in an ethyl acetate/tetrahydrofuran mixture, followed by washing with water. The organic phase was dried over anhydrous magnesium sulfate. The solvent was distilled off in vacuo, and the residue was purified by silica gel chromatography, thereby preparing 38 g of the title compound.

$^1H$—NMR ($CDCl_3$) δ: 1.24(6H, d, J=7 Hz), 1.36(6H, d, J=7 Hz), 1.36(3H, t, J=8 Hz), 3.2-3.6(2H, m), 3.70(3H, s), 4.30(2H, q, J=8 Hz), 7.40(1H, s), 7.50(2H, d, J=9 Hz), 7.98(2H, d, J=9 Hz)

EXAMPLE 34

2-(4-Carboxyphenylamino)-5,7-diisopropyl-6-methoxybenzothiazole

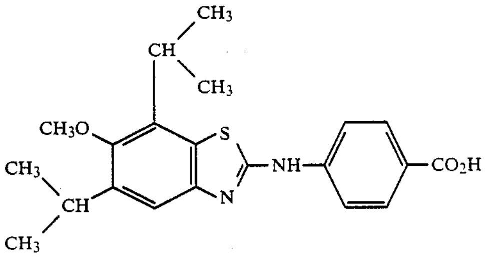

38 g of 5,7-diisopropyl-2-(4-ethoxycarbonyl)-6-methoxybenzothiazole prepared in Example 33 was dissolved in a mixed solvent comprising 100 ml of methanol and 100 ml of tetrahydrofuran. 30 ml of an aqueous 10N sodium hydroxide solution was added to the resulting solution, followed by heating under reflux for 1 hr. The reaction mixture was allowed to cool and then neutralized with 2N hydrochloric acid. The resulting crystal was separated by filtration, washed with water, and dried, thereby preparing 34 g of the title compound.

$^1H$—NMR ($CD_3OD$) δ: 1.26(6H, d, J=7 Hz), 1.36(6H, d, J=7 Hz), 3.2-3.6(2H, m), 3.72(3H, s), 7.28(1H, s), 7.66(2H, d, J=9 Hz), 7.94(2H, d, J=9 Hz)

EXAMPLE 35

The procedures described in Examples 32, 33, 34, and 7 or the procedure as described in Examples 32, 33, and 7 were successively conducted in that order to prepare compounds shown in Table 11.

TABLE 11

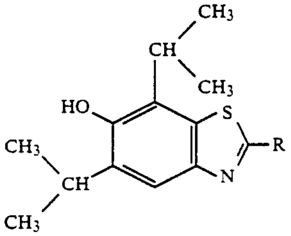

| Compd. No. | R | Salt | m.p. (°C.) | $^1$H-NMR |
|---|---|---|---|---|
| 113 | 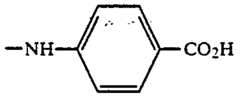 | hydrochloride | 195~197 | (DMSO-$d_6$)δ; 1.22(6H, d, J=7Hz), 1.28(6H, d, J=7Hz), 3.2~3.6(2H, m), 7.28(1H, s), 7.80(4H, m) |
| 114 | 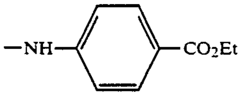 | hydrochloride | 148~150 | (DMSO-$d_6$)δ; 1.20(6H, d, J=7Hz), 1.30(6H, d, J=7Hz), 1.38(3H, t, J=8 Hz), 3.2~3.7(2H, m), 4.14(2H, q, J=8Hz), 7.24(1H, s), 7.80(4H, s) |
| 115 | 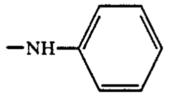 | hydrochloride | 173~175 | (DMSO-$d_6$)δ; 1.18(6H, d, J=7Hz), 1.28(6H, d, J=7Hz), 3.2~3.6(2H, m), 1.20(1H, s), 7.2~7.7(5H, m) |
| 116 | 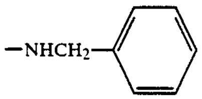 | hydrochloride | 201~204 | (DMSO-$d_6$)δ; 1.21(6H, d, J=7Hz), 1.34(6H, d, J=7Hz), 3.1~3.4(2H, m), 4.53(2H, s), 7.16(1H, s), 7.24(5H, s) |
| 117 | 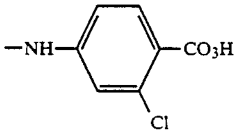 | hydrochloride | 218~220 | (DMSO-$d_6$)δ; 1.24(6H, d, J=7Hz), 1.32(6H, d, J=7Hz), 3.2~3.8(2H, m), 7.25(1H, s), 7.70(1H, dd, J=8Hz, 3Hz), 7.84(1H, d, J=8Hz), 8.40(1H, d, J=3Hz) |
| 118 | 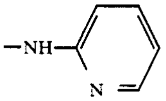 | free | 223~224 | (DMSO-$d_6$)δ; 1.22(6H, d, J=7Hz), 1.38(6H, d, J=7Hz), 3.1~3.8(2H, m), 6.8~7.2(2H, m), 7.23(1H, s), 7.60(1H, m), 8.30 (1H, m) |
| 119 | 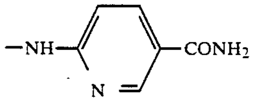 | free | 231~234 (dec.) | (DMSO-$d_6$)δ; 1.16(6H, d, J=7Hz), 1.35(6H, d, J=7Hz), 3.0~3.8(2H, m), 7.11(1H, d, J=9Hz), 7.21(1H, s), 8.05(1H, dd, J=9 Hz, 2Hz), 8.80(1H, d, J=2Hz) |
| 120 | 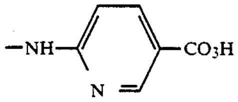 | free | 295~299 (dec.) | (DMSO-$d_6$)δ; 1.19(6H, d, J=7Hz), 1.34(6H, d, J=7Hz), 3.0~3.8(2H, m), 7.17(1H, d, J=10Hz), 7.23(1H, s), 8.07(1H, dd, J=10 Hz, 2Hz), 8.75(1H, d, J=2Hz) |
| 121 | 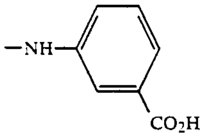 | free | 219~222 | (DMSO-$d_6$)δ; 1.17(6H, d, J=7Hz), 1.28(6H, d, J=7Hz), 3.1~3.7(2H, m), 7.20(1H, s), 7.3~7.6(2H, m), 7.80(1H, m), 8.22 (1H, m) |
| 122 | 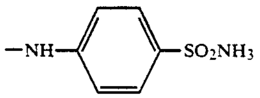 | free | 279~281 | (DMSO-$d_6$)δ; 1.20(6H, d, J=7Hz), 1.28(6H, d, J=7Hz), 3.2~3.6(2H, m), 7.24(1H, s), 7.66(2H, d, J=10Hz), 7.82(2H, d, J=10 Hz) |

TABLE 11-continued

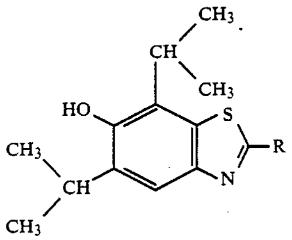

| Compd. No. | R | Salt | m.p. (°C.) | $^1$H-NMR |
|---|---|---|---|---|
| 123 | 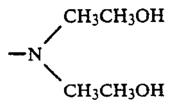 | hydrochloride | 171～173 | (DMSO-$d_6$)δ; 1.18(6H, d, J=7Hz), 1.28(6H, d, J=7Hz), 3.2～3.7(2H, m), 3.5～3.9(8H, m), 7.20(1H, s) |
| 124 | 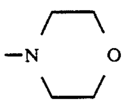 | hydrochloride | 170～172 | (DMSO-$d_6$)δ; 1.16(6H, d, J=7Hz), 1.28(6H, d, J=7Hz), 3.2～3.6(2H, m), 3.5～3.8(8H, m), 7.20(1H, s) |
| 125 | 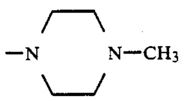 | free | 187～188 | (DMSO-$d_6$)δ; 1.24(6H, d, J=7Hz), 1.36(6H, d, J=7Hz), 2.30(3H, s), 2.48(4H, t, J=6Hz), 3.0～3.5(2H, m), 3.56(4H, t, J=6 Hz), 7.22(1H, s) |
| 126 | 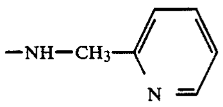 | free | 222～224 | (DMSO-$d_6$)δ; 1.12(6H, d, J=7Hz), 1.24(6H, d, J=7Hz), 3.2～3.6(2H, m), 1.56(2H, d, J=6Hz), 6.96(1H, s), 7.0～7.4(2H, m), 7.60(1H, dd, J=10Hz, 2Hz), 8.42(1H, d, J=5Hz) |
| 127 | 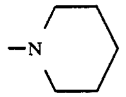 | free | 208～209 | ($CDCl_3$)δ; 1.24(6H, d, J=7Hz), 1.36(6H, d, J=7Hz), 1.5～1.8(6H, m), 3.0～3.4(2H, m), 3.4～3.6(4H, m), 7.20(1H, s) |
| 128 | 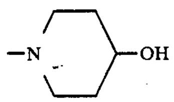 | free | 201～203 | (DMSO-$d_6$, $CDCl_3$)δ; 1.22(6H, d, J=7Hz), 1.34(6H, d, J=7Hz), 1.5～2.0(4H, m), 3.1～3.5(4H, m), 3.7～4.0(3H, m), 7.20(1H, s) |
| 129 | 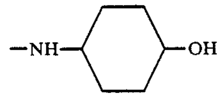 | hydrochloride | 247～251 (dec.) | (DMSO-$d_6$)δ; 1.16(6H, d, J=7Hz), 1.28(6H, d, J=7Hz), 1.1～1.5(4H, m), 1.7～2.1(4H, m), 3.3～3.6(4H, m), 7.20(1H, s) |
| 130 | 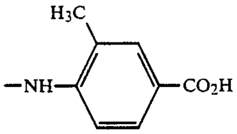 | free | 246～249 | ($CD_3OD$)δ; 1.26(6H, d, J=7Hz), 1.38(6H, d, J=7Hz), 2.36(3H, s), 3.3～3.7(2H, m), 7.24(1H, s), 7.76(1H, s), 7.82(1H, d, J=9Hz), 8.00(1H, d, J=9Hz) |
| 131 | 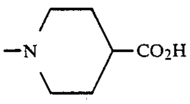 | free | 215～217 | (DMSO-$d_6$)δ; 1.18(6H, d, J=7Hz), 1.27(6H, d, J=8Hz), 1.4～2.0(4H, m), 2.50(1H, m), 2.9～4.0(6H, m), 7.07(1H, s) |
| 132 | 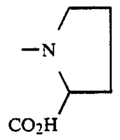 | free | 186～188 | (DMSO-$d_6$)δ; 1.18(6H, d, J=7Hz), 1.26(6H, d, J=7Hz), 1.8～2.3(4H, m), 3.0～3.8(4H, m), 4.36(1H, m), 7.02(1H, s) |

EXAMPLE 36

2-Benzylamino-6-hydroxy-4,5,7-trimethylbenzothiazole

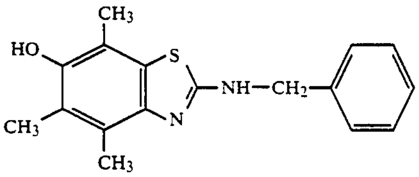

5.0 g of 2-amino-6-methoxy-4,5,7-trimethylbenzothiazole was dissolved in 100 ml of benzene. 5.9 g of benzaldehyde and 3.5 g of ammonium acetate were added to the resulting solution, followed by heating under reflux for 5 hr while removing the formed water with a water-withdrawing device. The reaction mixture was allowed to cool at room temperature, washed with water, and dried over anhydrous magnesium sulfate. Then the solvent was distilled off in vacuo. The residue was dissolved in 100 ml of ethanol. 1.5 g of sodium borohydride was added to the resulting solution while cooling the solution with ice. The mixture was stirred for 30 min. Ethanol was distilled off in vacuo and water was added to the residue, followed by extraction with ethyl acetate. The organic phase was washed with water and dried over anhydrous magnesium sulfate. The solvent was then distilled off in vacuo. The residue was treated in the same manner as that of Example 7, thereby preparing 4.9 g of the title compound.

$^1$H—NMR (DMSO—$d_6$) δ: 2.17(3H, s), 2.20(3H, s), 2.37(3H, s), 4.76(2H, s), 7.2–7.5(5H, m)

EXAMPLE 37

Compounds shown in Table 12 were prepared in the same manner as that of Example 36.

TABLE 12

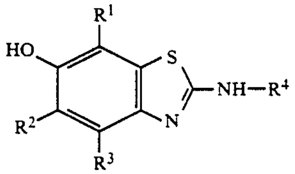

| Com-pd. No. | $R^1$ | $R^2$ | $R^3$ | $R^4$ | Salt | m.p. (°C.) | $^1$H-NMR |
|---|---|---|---|---|---|---|---|
| 133 | $CH_3$— | $CH_3$— | $CH_3$— | 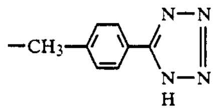 | HBr salt | 207~210 | (DMSO-$d_6$)δ; 2.14(3H, s), 2.18(3H, s), 2.28(3H, s), 4.76 (2H, s), 7.55(2H, d, J=10Hz), 7.96(2H, d, J=10 Hz) |
| 134 | $CH_3$— | $CH_3$— | $CH_3$— | 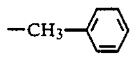 | hydro-chloride | 201~204 | (DMSO-$d_6$)δ; 2.17(3H, s), 2.20(3H, s), 2.37(3H, s), 4.76 (2H, s), 7.2~7.5(5H, m) |
| 135 | $CH_3$— | $CH_3$— | $CH_3$— | 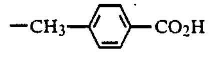 | free | >300 | (DMSO-$d_6$)δ; 2.12(3H, s), 2.18(3H, s), 2.34(3H, s), 4.56 (2H, d, J=6Hz), 7.40(2H, d, J=10Hz), 7.92(2H, d, J=10Hz) |
| 136 | $CH_3$— | $CH_3$— | $CH_3$— | 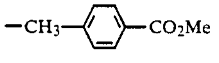 | hydro-chloride | 122~124 | (DMSO-$d_6$)δ; 2.13(3H, s), 2.18(3H, s), 2.36(3H, s), 3.80 (3H, s), 4.76(2H, s), 7.50(2H, d, J=10Hz), 7.87(2H, d, J=10Hz) |
| 137 | $CH_3$— | $CH_3$— | $CH_3$— | 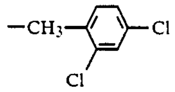 | hydro-chloride | 203~205 | (DMSO-$d_6$)δ; 2.16(3H, s), 2.22(3H, s), 2.37(3H, s), 4.76 (2H, s), 7.48(1H, d, J=3Hz), 7.54(1H, s), 7.68(1H, d, J=3Hz) |
| 138 | 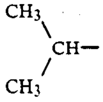 | 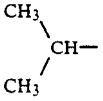 | H | 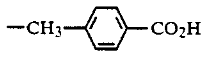 | free | 300> | (DMSO-$d_6$)δ; 1.15(6H, d, J=7Hz), 1.23(6H, d, J=7Hz), 3.2~3.7(2H, m), 4.60(2H, s), 6.98(1H, s), 7.39 (2H, d, J=9Hz), 7.83(2H, d, J=9Hz) |
| 139 | 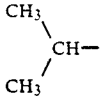 | 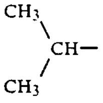 | H | 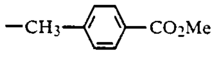 | free | 71~74 | ($CDCl_3$)δ; 1.24(6H, d, J=7Hz), 1.34(6H, d, J=7Hz), 3.1~3.4(2H, m), 3.86(3H, s), 4.63(2H, s), 7.17 (1H, s), 7.34(2H, d, J=9Hz), 7.91(2H, d, J=9Hz) |
| 140 | 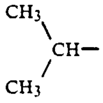 | 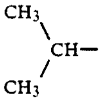 | H | 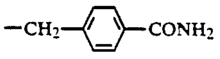 | free | 212~214 | (DMSO-$d_6$)δ; 1.16(6H, d, J=7Hz), 1.28(6H, d, J=7Hz), 3.2~3.6(2H, m), 4.60(2H, d, J=6Hz), 7.04(1H, s), 7.42(2H, d, J=10Hz), 7.86(2H, d, J=10Hz) |

TABLE 12-continued

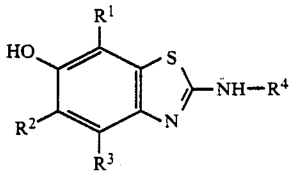

| Compd. No. | $R^1$ | $R^2$ | $R^3$ | $R^4$ | Salt | m.p. (°C.) | $^1$H-NMR |
|---|---|---|---|---|---|---|---|
| 141 | $CH_3$— | $CH_3$— | $CH_3$— | 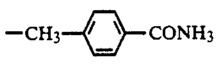 | hydrochloride | 231 ~ 235 (dec.) | ($DMSO-d_6$)δ; 2.16(3H, s), 2.22(3H, s), 2.40(3H, s), 4.86 (2H, s), 7.52(2H, d, J=9Hz), 7.92(2H, d, J=9Hz) |

We claim:

1. A benzothiazole compound having the formula:

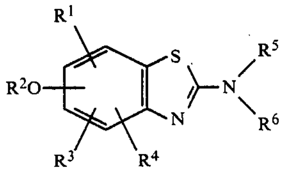

wherein $R^1$, $R^3$, and $R^4$ may be the same or different and are each a hydrogen atom, a lower alkyl group, a halogen atom, an acyl group, a hydroxyl group, a lower alkoxy group, a hydroxy lower alkyl group, a nitro group, an amino group, or a lower dialkylamino group, provided that any two of $R^1$, $R^3$ and $R^4$ may be combined together to form an aromatic ring which may consist of only carbon atoms or additionally contain a nitrogen atom, $R^2$ is a hydrogen atom, an acyl group, a group represented by the formula:

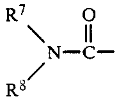

wherein $R^7$ and $R^8$ may be the same or different and are each a hydrogen atom or a lower alkyl group, $R^5$ is a hydrogen atom, and $R^6$ is a group represented by the formula:

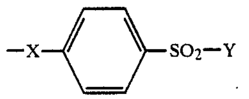

wherein X is a —CO— or a —$CH_2$—, and Y is a lower alkyl group or a group represented by the formula:

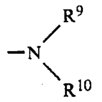

wherein $R^9$ and $R^{10}$ may be the same or different and are each a hydrogen atom, a lower alkyl group, a halogen atom, a lower alkoxy group, a hydroxy lower alkyl group or a lower dialkyl group or a pharmaceutically acceptable salt thereof.

2. The benzothiazole compound according to claim 1 having the formula:

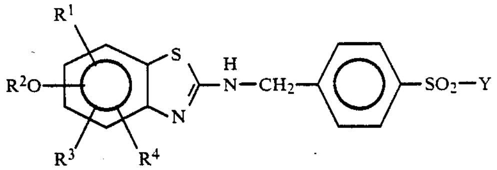

wherein $R^1$, $R^3$, and $R^4$ may be the same or different and are each a hydrogen atom, a lower alkyl group, a halogen atom, an acyl group, a hydroxyl group, a lower alkoxy group, a hydroxy lower alkyl group, a nitro group, an amino roup, or a lower dialkylamino group, provided that any two of $R^1$, $R^3$ and $R^4$ may be combined together to form an aromatic ring which may consist of only carbon atoms or additionally contain a nitrogen atom, $R^2$ is a hydrogen atom, an acyl group, a group represented by the formula:

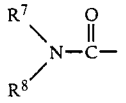

wherein $R^7$ and $R^8$ which may be the same or different are each a hydrogen atom or a lower alkyl group, and wherein Y is a lower alkyl group or a group represented by the formula:

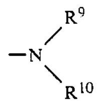

wherein $R^9$ and $R^{10}$ may be the same or different and are each a hydrogen atom, a lower alkyl group, a halogen atom, a lower alkoxy group, a hydroxy lower alkyl group, or a lower dialkyl group; or a pharmaceutically acceptable salt thereof.

3. The benzothiazole compound according to claim 1 having the formula:

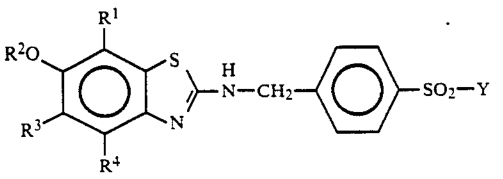

wherein $R^1$, $R^3$, and $R^4$ may be the same or different and are each a hydrogen atom, a lower alkyl group, a halogen atom, an acyl group, a hydroxyl group, a lower alkoxy group, a hydroxy lower alkyl group, a nitro group, an amino roup, or a lower dialkylamino group, provided that any two of $R^1$, $R^3$ and $R^4$ may be combined together to form an aromatic ring which may consist of only carbon atoms or additionally contain a nitrogen atom, $R^2$ is a hydrogen atom, an acyl group, a group represented by the formula:

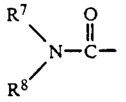

wherein $R^7$ and $R^8$ may be the same or different and are each a hydrogen atom or a lower alkyl group, and wherein Y is a lower alkyl group or a group represented by the formula:

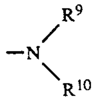

wherein $R^9$ and $R^{10}$ may be the same or different and are each a hydrogen atom, a lower alkyl group, a halogen atom, a lower alkoxy group, a hydroxy lower alkyl group or a lower dialkyl group; or a pharmaceutically acceptable salt thereof.

4. The benzothiazole compound according to claim 1 having the formula:

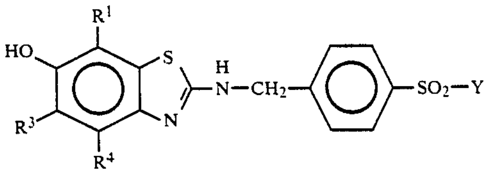

wherein $R^1$, $R^3$, and $R^4$ may be the same or different and are each a hydrogen atom, a lower alkyl group, a halogen atom, an acyl group, a hydroxyl group, a lower alkoxy group, a hydroxy lower alkyl group, a nitro group, an amino group, or a lower dialkylamino group, provided that any two of $R^1$, $R^3$ and $R^4$ may be combined together to form an aromatic ring which may consist of only carbon atoms or additionally contain a nitrogen atom; and wherein Y is a lower alkyl group or a group represented by the formula:

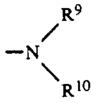

wherein $R^9$ and $R^{10}$ may be the same or different and are each a hydrogen atom, a lower alkyl group, a halogen atom, a lower alkoxy group, a hydroxy lower alkyl group or a lower dialkyl group; or a pharmaceutically acceptable salt thereof.

5. The benzothiazole compound according to claim 1 having the formula:

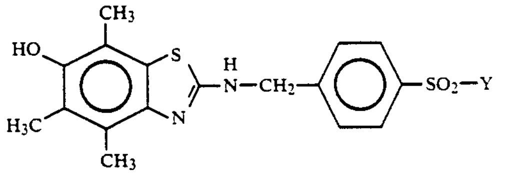

wherein Y is a lower alkyl group or a group represented by the formula:

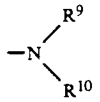

wherein $R^9$ and $R^{10}$ may be the same or different and are each a hydrogen atom, a lower alkyl group, a halogen atom, a lower alkoxy group, a hydroxy lower alkyl group, or a lower dialkyl group; or a pharmaceutically acceptable salt thereof.

6. A benzothiazole compound as claimed in claim 1 and a pharmacologically acceptable salt thereof, in which the benzothiazole ring has $R^{20}$— at 6-position.

7. A benzothiazole compound as claimed in claim 6 and a pharmacologically acceptable salt thereof, in which $R^2$ is hydrogen.

8. A benzothiazole compound as claimed in claim 6 or 7 and a pharmacologically acceptable salt thereof, in which $R^1$, $R^3$ and $R^4$ independently are hydrogen, a halogen or a lower alkyl.

9. A benzothiazole compound as claimed in claim 6 or 7 and a pharmacologically acceptable salt thereof, in which $R^1$, $R^3$ and $R^4$ independently are a lower alkyl.

10. A benzothiazole compound as claimed in claim 9 and a pharmacologically acceptable salt thereof, in which said lower alkyl is methyl.

11. A benzothiazole compound as claimed in claim 1 and a pharmacologically acceptable salt thereof, in which the benzothiazole has 5,7-diisopropyl and 6-hydroxy.

12. A benzothiazole compound as claimed in claim 1 and a pharmacologically acceptable salt thereof, in which —$OR^2$ is attached at 6-position to the ring, $R^2$ is hydrogen, $R^1$, $R^3$ and $R^4$ independently are hydrogen, a halogen or a lower alkyl, $R^5$ is hydrogen and $R^6$ is (2).

13. A benzothiazole compound as claimed in claim 12 and a pharmacologically acceptable salt thereof, in which X is methylene.

14. A benzothiazole compound as claimed in claim 12 and a pharmacologically acceptable salt thereof, in which X is —CO—.

15. A benzothiazole compound as claimed in claim 12 and a pharmacologically acceptable salt thereof, in which X is methylene and Y is amino.

16. A benzothiazole compound as claimed in claim 1 and a pharmacologically acceptable salt thereof, which is 6-hydroxy-2-(4-sulfamoylbenzylamino)-4,5,7-trimethylbenzothiazole.

17. The benzothiazole compound according to claim 1 wherein said acyl group is an aliphatic group, aromatic ring or heterocyclic ring.

18. A benzothiazole compound as claimed in claim 1 and a pharmacologically acceptable salt thereof, which is selected from the group consisting of:

6-hydroxy-2-(4-carboxylphenylamino)-4,5,7-trimethylbenzothiazole,
6-hydroxy-2-amino-4,5,7-trimethylbenzothiazole,
6-hydroxy-2-(4-carboxylphenylamino)-5,7-diisopropylbenzothiazole,
6-hydroxy-2-(N,N-di(2-hydroxyethyl)amino)-5,7-diisopropylbenzothiazole,
6-hydroxy-2-(2-pyridylmethylamino)-5,7-diisopropylbenzothiazole,
6-hydroxy-2-(4-sulfamoylbenzylamino)-5,7-dibromobenzothiazole and
4-hydroxy-2-(4-sulfamoylbenzylamino)-5,7-dibromobenzothiazole.

19. The benzothiazole according to claim 18 which is 6-hydroxy-2-(4-sulfamoylbenzylamino)-5,7-dibromobenzothiazole.

20. The benzothiazole according to claim 18 which is 4-hydroxy-2-(4-sulfamoylamino)-5,7-dibromobenzothiazole.

21. A pharmaceutical composition for treating a disease caused by leukotriene production which comprises an anti-leukotriene producing amount of the benzothiazole compound as defined in claim 1 or a pharmacologically acceptable salt thereof and a pharmacologically acceptable carrier.

22. A method for treating disease caused by production of leukotriene, by administering to a human patient in need thereof a therapeutically effective amount of a benzothiazole compound as defined in claim 1 or a pharmacologically acceptable salt thereof.

23. The method as claimed in claim 22, in which the desease is asthma.

24. The method according to claim 22 wherein said disease is an affection of the skin.

25. The method according to claim 22 wherein said disease is an allergic disease.

26. The method according to claim 24 wherein said affection of the skin is psoriasis or eczema.

27. The method according to claim 25 wherein said allergic disease is allergic rhinitis.

* * * * *